US008710211B2

(12) United States Patent
Brahmasandra et al.

(10) Patent No.: US 8,710,211 B2
(45) Date of Patent: *Apr. 29, 2014

(54) POLYNUCLEOTIDE CAPTURE MATERIALS, AND METHODS OF USING SAME

(71) Applicant: HandyLab, Inc., Ann Arbor, MI (US)

(72) Inventors: Sundaresh N. Brahmasandra, Ann Arbor, MI (US); Elizabeth Craig, Ypsilanti, MI (US)

(73) Assignee: Handylab, Inc., Ann Arbor, MI (US)

(\*) Notice: Subject to any disclaimer, the term of this patent is extended or adjusted under 35 U.S.C. 154(b) by 0 days.

This patent is subject to a terminal disclaimer.

(21) Appl. No.: 13/692,980

(22) Filed: Dec. 3, 2012

(65) Prior Publication Data

US 2013/0096292 A1  Apr. 18, 2013

Related U.S. Application Data

(63) Continuation of application No. 12/172,214, filed on Jul. 11, 2008, now Pat. No. 8,324,372.

(60) Provisional application No. 60/959,437, filed on Jul. 13, 2007.

(51) Int. Cl.
C07H 21/00 (2006.01)

(52) U.S. Cl.
USPC .................... 536/25.4; 536/25.41; 536/25.42

(58) Field of Classification Search
None
See application file for complete search history.

(56) References Cited

U.S. PATENT DOCUMENTS

| | | |
|---|---|---|
| 1,434,314 A | 10/1922 | Raich |
| 1,616,419 A | 2/1927 | Wilson |
| 1,733,401 A | 8/1930 | Lovekin |
| D189,404 S | 12/1960 | Nicolle |
| 3,528,449 A | 9/1970 | Witte et al. |
| 3,813,316 A | 5/1974 | Chakrabarty et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Teraski et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Schiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler et al. |
| 4,963,498 A | 10/1990 | Hillman |
| 4,967,950 A | 11/1990 | Legg et al. |

(Continued)

FOREIGN PATENT DOCUMENTS

| | | |
|---|---|---|
| CA | 2294819 | 1/1999 |
| DE | 19929734 | 12/1999 |

(Continued)

OTHER PUBLICATIONS

Bollet, C. et al., "A simple method for the isolation of chromosomal DNA from Gram positive or acid-fast bacteria", Nucleic Acids Research, vol. 19, No. 8 (1991), p. 1955.

Brahmassandra, et al., On-Chip DNA Detection in Microfabricated Separation Systems, Part of the SPIE Conference on Microfluidic Devices and Systems, 1998, Santa Clara, California, vol. 3515, pp. 242-251.

Breadmore et al., "Microchip-Based Purification of DNA from Biological Samples", Anal. Chem., vol. 75 (2003), pp. 1880-1886.

(Continued)

*Primary Examiner* — Lawrence E Crane

(74) *Attorney, Agent, or Firm* — Knobbe Martens Olson & Bear LLP

(57) ABSTRACT

Methods for processing polynucleotide-containing biological samples, and materials for capturing polynucleotide molecules such as RNA and/or DNA from such samples. The RNA and/or DNA is captured by polyamindoamine (PAMAM (Generation 0)) bound to a surface, such as the surface of magnetic particles. The methods and materials have high efficiency of binding RNA and of DNA, and of release, and thereby permit quantitative determinations.

12 Claims, 9 Drawing Sheets

(56) References Cited

U.S. PATENT DOCUMENTS

| | | |
|---|---|---|
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,223,226 A | 6/1993 | Wittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic, Jr. |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson et al. |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,585,069 A | 12/1996 | Zanzucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,726,026 A | 3/1998 | Wilding et al. |
| 5,726,404 A | 3/1998 | Brody |
| 5,726,944 A | 3/1998 | Taft et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |

(56) References Cited

U.S. PATENT DOCUMENTS

| | | |
|---|---|---|
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| D438,311 S | 2/2001 | Yamanishi et al. |
| 6,190,619 B1 | 2/2001 | Kilcoin et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | MacLeod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,287,254 B1 | 9/2001 | Dodds |
| 6,287,774 B1 | 9/2001 | Kikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-Sill |
| 6,306,273 B1 | 10/2001 | Wainright et al. |
| 6,306,590 B1 | 10/2001 | Mehta et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-Sill et al. |
| 6,366,924 B1 | 4/2002 | Parce |
| 6,368,871 B1 | 4/2002 | Christel et al. |
| 6,370,206 B1 | 4/2002 | Schenk |

(56) References Cited

U.S. PATENT DOCUMENTS

| | | |
|---|---|---|
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Majer et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-Sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-Sill et al. |
| D470,595 S | 2/2003 | Crisanti et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-Sill et al. |
| D472,324 S | 3/2003 | Rumore et al. |
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| D474,279 S | 5/2003 | Mayer et al. |
| D474,280 S | 5/2003 | Niedbala et al. |
| 6,558,916 B2 | 5/2003 | Veerapandian et al. |
| 6,558,945 B1 | 5/2003 | Kao |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | McCormick et al. |
| 6,613,512 B1 | 9/2003 | Kopf-Sill et al. |
| 6,613,580 B1 | 9/2003 | Chow et al. |
| 6,613,581 B1 | 9/2003 | Wada et al. |
| 6,614,030 B2 | 9/2003 | Maher et al. |
| 6,620,625 B2 | 9/2003 | Wolk et al. |
| 6,623,860 B2 | 9/2003 | Hu et al. |
| 6,627,406 B1 | 9/2003 | Singh et al. |
| D480,814 S | 10/2003 | Lafferty et al. |
| 6,632,655 B1 | 10/2003 | Mehta et al. |
| D482,796 S | 11/2003 | Oyama et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| D484,989 S | 1/2004 | Gebrian |
| 6,681,616 B2 | 1/2004 | Spaid et al. |
| 6,681,788 B2 | 1/2004 | Parce et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,720,148 B1 | 4/2004 | Nikiforov |
| 6,730,206 B2 | 5/2004 | Ricco et al. |
| 6,733,645 B1 | 5/2004 | Chow |
| 6,734,401 B2 | 5/2004 | Bedingham et al. |
| 6,740,518 B1 | 5/2004 | Duong et al. |
| D491,272 S | 6/2004 | Alden et al. |
| D491,273 S | 6/2004 | Biegler et al. |
| D491,276 S | 6/2004 | Langille |
| 6,750,661 B2 | 6/2004 | Brooks et al. |
| 6,752,966 B1 | 6/2004 | Chazan |
| 6,756,019 B1 | 6/2004 | Dubrow et al. |
| 6,766,817 B2 | 7/2004 | da Silva |
| 6,773,567 B1 | 8/2004 | Wolk |
| 6,777,184 B2 | 8/2004 | Nikiforov et al. |
| 6,783,962 B1 | 8/2004 | Olander et al. |
| D495,805 S | 9/2004 | Lea et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D499,813 S | 12/2004 | Wu |
| D500,142 S | 12/2004 | Crisanti et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,838,680 B2 | 1/2005 | Maher et al. |
| 6,852,287 B2 | 2/2005 | Ganesan |
| 6,858,185 B1 | 2/2005 | Kopf-Sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,900,889 B2 | 5/2005 | Bjornson et al. |
| 6,905,583 B2 | 6/2005 | Wainright et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| D508,999 S | 8/2005 | Fanning et al. |
| 6,939,451 B2 | 9/2005 | Zhao et al. |
| 6,942,771 B1 | 9/2005 | Kayyem |
| 6,958,392 B2 | 10/2005 | Fomovskaia et al. |
| D512,155 S | 11/2005 | Matsumoto |
| 6,964,747 B2 | 11/2005 | Banerjee et al. |
| 6,977,163 B1 | 12/2005 | Mehta |
| 6,984,516 B2 | 1/2006 | Briscoe et al. |
| D515,707 S | 2/2006 | Shinohara et al. |

(56) References Cited

U.S. PATENT DOCUMENTS

| | | |
|---|---|---|
| D516,221 S | 2/2006 | Wohlstadter et al. |
| 7,001,853 B1 | 2/2006 | Brown et al. |
| 7,004,184 B2 | 2/2006 | Handique et al. |
| D517,554 S | 3/2006 | Yanagisawa et al. |
| 7,010,391 B2 | 3/2006 | Handique et al. |
| 7,023,007 B2 | 4/2006 | Gallagher |
| 7,024,281 B1 | 4/2006 | Unno |
| 7,036,667 B2 | 5/2006 | Greenstein et al. |
| 7,037,416 B2 | 5/2006 | Parce et al. |
| 7,038,472 B1 | 5/2006 | Chien |
| 7,039,527 B2 | 5/2006 | Tripathi et al. |
| 7,040,144 B2 | 5/2006 | Spaid et al. |
| 7,049,558 B2 | 5/2006 | Baer et al. |
| D523,153 S | 6/2006 | Akashi et al. |
| 7,055,695 B2 | 6/2006 | Greenstein et al. |
| 7,060,171 B1 | 6/2006 | Nikiforov et al. |
| 7,066,586 B2 | 6/2006 | da Silva |
| 7,069,952 B1 | 7/2006 | McReynolds et al. |
| 7,099,778 B2 | 8/2006 | Chien |
| D528,215 S | 9/2006 | Malmsater |
| 7,101,467 B2 | 9/2006 | Spaid |
| 7,105,304 B1 | 9/2006 | Nikiforov et al. |
| D531,321 S | 10/2006 | Godfrey et al. |
| 7,118,910 B2 | 10/2006 | Unger et al. |
| 7,138,032 B2 | 11/2006 | Gandhi et al. |
| D534,280 S | 12/2006 | Gomm et al. |
| 7,148,043 B2 | 12/2006 | Kordunsky et al. |
| 7,150,814 B1 | 12/2006 | Parce et al. |
| 7,150,999 B1 | 12/2006 | Shuck |
| D535,403 S | 1/2007 | Isozaki et al. |
| 7,160,423 B2 | 1/2007 | Chien et al. |
| 7,161,356 B1 | 1/2007 | Chien |
| 7,169,277 B2 | 1/2007 | Ausserer et al. |
| 7,169,618 B2 | 1/2007 | Skold |
| D537,951 S | 3/2007 | Okamoto et al. |
| D538,436 S | 3/2007 | Patadia et al. |
| 7,192,557 B2 | 3/2007 | Wu et al. |
| 7,195,986 B1 | 3/2007 | Bousse et al. |
| 7,208,125 B1 | 4/2007 | Dong |
| 7,235,406 B1 | 6/2007 | Woudenberg et al. |
| 7,247,274 B1 | 7/2007 | Chow |
| D548,841 S | 8/2007 | Brownell et al. |
| D549,827 S | 8/2007 | Maeno et al. |
| 7,252,928 B1 | 8/2007 | Hafeman et al. |
| 7,270,786 B2 | 9/2007 | Parunak et al. |
| D554,069 S | 10/2007 | Bolotin et al. |
| D554,070 S | 10/2007 | Bolotin et al. |
| 7,276,330 B2 | 10/2007 | Chow et al. |
| D556,914 S | 12/2007 | Okamoto et al. |
| 7,303,727 B1 | 12/2007 | Dubrow et al. |
| D559,995 S | 1/2008 | Handique et al. |
| 7,323,140 B2 | 1/2008 | Handique et al. |
| 7,332,130 B2 | 2/2008 | Handique |
| 7,338,760 B2 | 3/2008 | Gong et al. |
| D566,291 S | 4/2008 | Parunak et al. |
| 7,351,377 B2 | 4/2008 | Chazan et al. |
| D569,526 S | 5/2008 | Duffy et al. |
| 7,374,949 B2 | 5/2008 | Kuriger |
| 7,390,460 B2 | 6/2008 | Osawa et al. |
| 7,419,784 B2 | 9/2008 | Dubrow et al. |
| 7,422,669 B2 | 9/2008 | Jacobson et al. |
| 7,440,684 B2 | 10/2008 | Spaid et al. |
| 7,476,313 B2 | 1/2009 | Siddiqi |
| 7,494,577 B2 | 2/2009 | Williams et al. |
| 7,494,770 B2 | 2/2009 | Wilding et al. |
| 7,514,046 B2 | 4/2009 | Kechagia et al. |
| 7,518,726 B2 | 4/2009 | Rulison et al. |
| 7,521,186 B2 | 4/2009 | Burd Mehta |
| 7,527,769 B2 | 5/2009 | Bunch et al. |
| 7,553,671 B2 | 6/2009 | Sinclair |
| D596,312 S | 7/2009 | Giraud et al. |
| 7,595,197 B2 | 9/2009 | Brasseur |
| 7,604,938 B2 | 10/2009 | Takahashi et al. |
| 7,635,588 B2 | 12/2009 | King et al. |
| 7,645,581 B2 | 1/2010 | Knapp et al. |
| 7,670,559 B2 | 3/2010 | Chien et al. |
| 7,674,431 B2 | 3/2010 | Ganesan |
| 7,704,735 B2 | 4/2010 | Facer et al. |
| 7,723,123 B1 | 5/2010 | Murphy et al. |
| D618,820 S | 6/2010 | Wilson et al. |
| 7,727,371 B2 | 6/2010 | Kennedy et al. |
| 7,727,477 B2 | 6/2010 | Boronkay et al. |
| 7,744,817 B2 | 6/2010 | Bui |
| 7,867,776 B2 | 1/2011 | Kennedy et al. |
| 7,892,819 B2 | 2/2011 | Wilding et al. |
| D637,737 S | 5/2011 | Wilson et al. |
| 7,998,708 B2 | 8/2011 | Handique et al. |
| 8,133,671 B2 | 3/2012 | Williams et al. |
| 8,182,763 B2 | 5/2012 | Duffy et al. |
| 8,273,308 B2 | 9/2012 | Handique et al. |
| D669,597 S | 10/2012 | Cavada et al. |
| 8,323,584 B2 | 12/2012 | Ganesan |
| 8,323,900 B2 | 12/2012 | Handique et al. |
| 8,324,372 B2 * | 12/2012 | Brahmasandra et al. .... 536/25.4 |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D692,162 S | 10/2013 | Lentz et al. |
| 2001/0012492 A1 | 8/2001 | Acosta et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0046702 A1 | 11/2001 | Schembri |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2003/0019522 A1 | 1/2003 | Parunak |
| 2003/0049174 A1 | 3/2003 | Ganesan |
| 2003/0049833 A1 | 3/2003 | Chen et al. |
| 2003/0064507 A1 | 4/2003 | Gallagher et al. |
| 2003/0070677 A1 | 4/2003 | Handique et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014238 A1 | 1/2004 | Krug et al. |
| 2004/0018119 A1 | 1/2004 | Massaro |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0086427 A1 | 5/2004 | Childers et al. |
| 2004/0086956 A1 | 5/2004 | Bachur, Jr. |
| 2004/0141887 A1 | 7/2004 | Mainquist et al. |
| 2004/0151629 A1 | 8/2004 | Pease et al. |

(56) References Cited

U.S. PATENT DOCUMENTS

| | | |
|---|---|---|
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-Sill et al. |
| 2005/0152808 A1 | 7/2005 | Ganesan |
| 2005/0170362 A1 | 8/2005 | Wada et al. |
| 2005/0186585 A1 | 8/2005 | Juncosa et al. |
| 2005/0202470 A1 | 9/2005 | Sundberg et al. |
| 2005/0202504 A1 | 9/2005 | Anderson et al. |
| 2005/0208676 A1 | 9/2005 | Kahatt |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0238545 A1 | 10/2005 | Parce et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0062696 A1 | 3/2006 | Chow et al. |
| 2006/0094108 A1 | 5/2006 | Yoder et al. |
| 2006/0113190 A1 | 6/2006 | Kurnik |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0165559 A1 | 7/2006 | Greenstein et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0207944 A1 | 9/2006 | Siddiqi |
| 2006/0210435 A1 | 9/2006 | Alavie et al. |
| 2006/0246493 A1 | 11/2006 | Jensen et al. |
| 2006/0246533 A1 | 11/2006 | Fathollahi et al. |
| 2007/0004028 A1 | 1/2007 | Lair et al. |
| 2007/0009386 A1 | 1/2007 | Padmanabhan et al. |
| 2007/0020699 A1 | 1/2007 | Carpenter et al. |
| 2007/0026421 A1 | 2/2007 | Sundberg et al. |
| 2007/0042441 A1 | 2/2007 | Masters et al. |
| 2007/0092901 A1 | 4/2007 | Ligler et al. |
| 2007/0098600 A1 | 5/2007 | Kayyem et al. |
| 2007/0099200 A1 | 5/2007 | Chow et al. |
| 2007/0104617 A1 | 5/2007 | Coulling et al. |
| 2007/0154895 A1 | 7/2007 | Spaid et al. |
| 2007/0177147 A1 | 8/2007 | Parce |
| 2007/0178607 A1 | 8/2007 | Prober et al. |
| 2007/0184463 A1 | 8/2007 | Molho et al. |
| 2007/0184547 A1 | 8/2007 | Handique et al. |
| 2007/0196238 A1 | 8/2007 | Kennedy et al. |
| 2007/0199821 A1 | 8/2007 | Chow |
| 2007/0215554 A1 | 9/2007 | Kreuwel et al. |
| 2007/0218459 A1 | 9/2007 | Miller et al. |
| 2007/0231213 A1 | 10/2007 | Prabhu et al. |
| 2007/0243626 A1 | 10/2007 | Windeyer et al. |
| 2007/0261479 A1 | 11/2007 | Spaid et al. |
| 2007/0269861 A1 | 11/2007 | Williams et al. |
| 2007/0292941 A1 | 12/2007 | Handique et al. |
| 2008/0000774 A1 | 1/2008 | Park et al. |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1 | 3/2008 | McNeely |
| 2008/0075634 A1 | 3/2008 | Herchenbach et al. |
| 2008/0090244 A1 | 4/2008 | Knapp et al. |
| 2008/0095673 A1 | 4/2008 | Xu |
| 2008/0118987 A1 | 5/2008 | Eastwood et al. |
| 2008/0124723 A1 | 5/2008 | Dale et al. |
| 2008/0149840 A1 | 6/2008 | Handique et al. |
| 2008/0160601 A1 | 7/2008 | Handique |
| 2008/0182301 A1 | 7/2008 | Handique et al. |
| 2008/0192254 A1 | 8/2008 | Kim et al. |
| 2008/0226502 A1 | 9/2008 | Jonsmann et al. |
| 2008/0247914 A1 | 10/2008 | Edens et al. |
| 2008/0262213 A1 | 10/2008 | Wu et al. |
| 2009/0047713 A1 | 2/2009 | Handique |
| 2009/0129978 A1 | 5/2009 | Wilson et al. |
| 2009/0130719 A1 | 5/2009 | Handique |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0136386 A1 | 5/2009 | Duffy et al. |
| 2009/0155123 A1 | 6/2009 | Williams et al. |
| 2009/0189089 A1 | 7/2009 | Bedingham et al. |
| 2009/0221059 A1 | 9/2009 | Williams et al. |
| 2009/0223925 A1 | 9/2009 | Morse et al. |
| 2010/0173393 A1 | 7/2010 | Handique et al. |
| 2011/0008825 A1 | 1/2011 | Ingber et al. |
| 2011/0027151 A1 | 2/2011 | Handique et al. |
| 2011/0207140 A1 | 8/2011 | Handique et al. |
| 2011/0210257 A9 | 9/2011 | Handique et al. |
| 2012/0022695 A1 | 1/2012 | Handique et al. |
| 2012/0085416 A1 | 4/2012 | Ganesan |
| 2012/0122108 A1 | 5/2012 | Handique |
| 2012/0160826 A1 | 6/2012 | Handique |
| 2012/0171759 A1 | 7/2012 | Williams et al. |
| 2012/0183454 A1 | 7/2012 | Handique |
| 2013/0037564 A1 | 2/2013 | Williams et al. |
| 2013/0071851 A1 | 3/2013 | Handique et al. |
| 2013/0101990 A1 | 4/2013 | Handique et al. |
| 2013/0164832 A1 | 6/2013 | Ganesan et al. |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |

FOREIGN PATENT DOCUMENTS

| | | |
|---|---|---|
| EP | 0766256 | 4/1997 |
| EP | 1541237 A2 | 6/2005 |
| EP | 2372367 A1 | 10/2011 |
| FR | 2672301 | 8/1992 |
| FR | 2795426 | 12/2000 |
| JP | 58212921 A | 12/1983 |
| JP | H07-290706 | 11/1995 |
| JP | 2001-509437 | 7/2001 |
| JP | 2001-515216 | 9/2001 |
| JP | 2001-527220 | 12/2001 |
| JP | 2002-503331 | 1/2002 |
| JP | 2002-215241 | 7/2002 |
| JP | 2003-500674 | 1/2003 |
| JP | 2005-514718 | 5/2005 |
| JP | 2005-518825 | 6/2005 |
| JP | 2005-204661 | 8/2005 |
| JP | 2005-291954 A | 10/2005 |
| JP | 2005-532043 | 10/2005 |
| WO | WO 88/06633 | 9/1988 |
| WO | WO 90/12350 | 10/1990 |
| WO | WO 92/05443 | 4/1992 |
| WO | WO 96/04547 | 2/1996 |
| WO | WO 97/05492 | 2/1997 |
| WO | WO 97/21090 | 6/1997 |
| WO | WO 98/00231 | 1/1998 |
| WO | WO 98/22625 | 5/1998 |
| WO | WO 98/49548 | 11/1998 |
| WO | WO 98/53311 | 11/1998 |
| WO | WO 99/01688 | 1/1999 |
| WO | WO 99/09042 | 2/1999 |

(56) References Cited

FOREIGN PATENT DOCUMENTS

| | | |
|---|---|---|
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 03/076661 | 9/2003 |
| WO | WO 2004/007081 | 1/2004 |
| WO | WO 2004/055522 | 7/2004 |
| WO | WO 2004/074848 | 9/2004 |
| WO | WO 2005/011867 | 2/2005 |
| WO | WO 2005/108620 | 11/2005 |
| WO | WO 2006/079082 | 7/2006 |
| WO | WO 2006/119280 | 11/2006 |
| WO | WO 2007/044917 | 4/2007 |
| WO | WO 2007/050327 | 5/2007 |
| WO | WO 2008/030914 | 3/2008 |
| WO | WO 2008/060604 | 5/2008 |
| WO | WO 2009/012185 | 1/2009 |
| WO | WO 2010/118541 | 10/2010 |

OTHER PUBLICATIONS

Brody et al., Diffusion-Based Extraction in a Microfabricated Device, Sensors and Actuators Elsevier, 1997, vol. A58, No. 1, pp. 13-18.
Broyles et al., "Sample Filtration, Concentration, and Separation Integrated on Microfluidic Devices" Analytical Chemistry (American Chemical Society), (2003) 75(11): 2761-2767.
Burns et al., "An Integrated Nanoliter DNA Analysis Device", Science 282:484-487 (1998).
Carlen et al., "Paraffin Actuated Surface Micromachined Valve," in IEEE MEMS 2000 Conference, p. 381-385, Miyazaki, Japan, Jan. 2000.
Chung, Y. et al., "Microfluidic chip for high efficiency DNA extraction", Miniaturisation for Chemistry, Biology & Bioengineering, vol. 4, No. 2 (Apr. 2004), pp. 141-147.
Handique et al, "Microfluidic flow control using selective hydrophobic patterning", SPIE, vol. 3224, pp. 185-194 (1997).
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromech. Microeng., 11:548-554 (2001).
Handique et al., "Nanoliter Liquid Metering in Microchannels Using Hydrophobic Patterns", Anal. Chem., 72:4100-4109 (2000).
Handique et al., On-Chip Thermopneumatic Pressure for Discrete Drop Pumping, Analytical Chemistry, American Chemical Society, Apr. 15, 2001, vol. 73, No. 8, 1831-1838.
He et al., Microfabricated Filters for Microfluidic Analytical Systems, Analytical Chemistry, American Chemical Society, 1999, vol. 71, No. 7, pp. 1464-1468.
Ibrahim et al., Real-Time Microchip PCR for Detecting Single-Base Differences in Viral and Human DNA, Analytical Chemistry, American Chemical Society, 1998, vol. 70, No. 9, pp. 2013-2017.
Khandurina et al., Microfabricated Porous Membrane Structure for Sample Concentration and Electrophoretic Analysis, Analytical Chemistry American Chemical Society, 1999, vol. 71, No. 9, pp. 1815-1819.
Kopp et al., Chemical Amplification: Continuous-Flow PCR on a Chip, www.sciencemag.org, 1998, vol. 280, pp. 1046-1048.
Kutter et al., Solid Phase Extraction on Microfluidic Devices, J. Microcolumn Separations, John Wiley & Sons, Inc., 2000, vol. 12, No. 2, pp. 93-97.
Lagally et al., Single-Molecule DNA Amplification and Analysis in an Integrated Microfluidic Device, Analytical Chemistry, American Chemical Society, 2001, vol. 73, No. 3 pp. 565-570.
Livache et al., "Polypyrrole DNA chip on a Silicon Device: Example of Hepatitis C Virus Genotyping", Analytical Biochemistry, vol. 255 (1998), pp. 188-194.
Mascini et al., "DNA electrochemical biosensors", Fresenius J. Anal. Chem., 369: 15-22, (2001).
Nakagawa et al., Fabrication of amino silane-coated microchip for DNA extraction from whole blood, J of Biotechnology, Mar. 2, 2005, vol. 116, pp. 105-111.
Northrup et al., A Miniature Analytical Instrument for Nucleic Acids Based on Micromachined Silicon Reaction Chambers, Analytical Chemistry, American Chemical Society, 1998, vol. 70, No. 5, pp. 918-922.
Oleschuk et al., Trapping of Bead-Based Reagents within Microfluidic Systems,: On-Chip Solid-Phase Extraction and Electrochromatography, Analytical Chemistry, American Chemical Society, 2000, vol. 72, No. 3, pp. 585-590.
Plambeck et al., "Electrochemical Studies of Antitumor Antibiotics", J. Electrochem Soc.: Electrochemical Science and Technology (1984), 131(11): 2556-2563.
Roche et al. "Ectodermal commitment of insulin-producing cells derived from mouse embryonic stem cells" Faseb J (2005) 19: 1341-1343.
Ross et al., Analysis of DNA Fragments from Conventional and Microfabricated PCR Devices Using Delayed Extraction MALDI-TOF Mass Spectrometry, Analytical Chemistry, American Chemical Society, 1998, vol. 70, No. 10, pp. 2067-2073.
Shoffner et al., Chip PCR.I. Surface Passivation of Microfabricated Silicon-Glass Chips for PCR, Nucleic Acids Research, Oxford University Press, 1996, vol. 24, No. 2, 375-379.
Smith et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Wang, "Survey and Summary, from DNA Biosensors to Gene Chips", Nucleic Acids Research, 28(16):3011-3016, (2000).
Waters et al., Microchip Device for Cell Lysis, Multiplex PCR Amplification, and Electrophoretic Sizing, Analytical Chemistry, American Chemical Society, 1998, vol. 70, No. 1, pp. 158-162.
Weigl et al., Microfluidic Diffusion-Based Separation and Detection, www.sciencemag.org, 1999, vol. 283, pp. 346-347.
Yoza et al., "Fully Automated DNA Extraction from Blood Using Magnetic Particles Modified with a Hyperbranched Polyamidomine Dendrimer", Journal of Bioscience and Bioengineering, 95(1):21-26, 2003.
Yoza et al., DNA extraction using bacterial magnetic particles modified with hyperbranched polyamidoamine dendrimer, Mar. 20, 2003, 101(3): 219-228.
International Search Report and Written Opinion, dated Oct. 3, 2008, issued in International Application No. PCT/US2008/069897, filed Jul. 11, 2008.
International Search Report dated Jun. 17, 2009 for Application No. PCT/US2008/008640, filed Jul. 14, 2008.
International Preliminary Report on Patentability dated Jan. 19, 2010 for Application No. PCT/US2008/069897, filed Jul. 11, 2008.
International Preliminary Report on Patentability and Written Opinion dated Jan. 19, 2010 for Application No. PCT/US2008/008640, filed Jul. 14, 2008.
European Supplemental Search Report dated Aug. 5, 2010 for Application No. EP 08826342.1, filed Jul. 11, 2008.
European Supplemental Search Report dated Jul. 13, 2012 for Application No. EP 08843060.8, filed Jul. 14, 2008.

\* cited by examiner

EV13 RNA EXTRACTION IN NASAL SWAB COLLECTED IN M4 MEDIA; RNA SPIKED INTO NASAL SWAB SAMPLES AT 1000, 100, AND 50 COPIES PER 1mL SAMPLE

DNA EXTRACTION USING RNA BEADS; 2.5 pg DNA SPIKED INTO M4 OR COLLECTION BUFFER AND EXTRACTED USING RNA BEAD PROTOCOL

POLYNUCLEOTIDE CAPTURE MATERIALS, AND METHODS OF USING SAME

CLAIM OF PRIORITY

This application is a continuation application of application Ser. No. 12/172,214, now U.S. Pat. No. 8,324,372, filed on Jul. 11, 2008, which claims the benefit of priority under 35 U.S.C. §119(e) to U.S. provisional application Ser. No. 60/959,437, filed Jul. 13, 2007, which is incorporated herein by reference in its entirety.

TECHNICAL FIELD

The technology described herein generally relates to methods for processing biological samples, and more particularly relates to materials for capturing polynucleotide molecules such as RNA and DNA from such samples, and permitting quantitative determination thereof.

BACKGROUND OF THE INVENTION

Field of the Invention

The analysis of a biological sample such as a clinical sample or a test sample of food, for presence of a pathogen such as a virus, or to determine the presence of a particular gene, will typically include detecting one or more polynucleotides present in the sample. One type of detection is qualitative detection, which relates to a determination of the presence or absence of a target polynucleotide and/or the determination of information related to, for example, the type, size, presence or absence of mutations, and/or the sequence of the target polynucleotide. Another type of detection is quantitative detection, which relates to a determination of the amount of a particular polynucleotide present in the sample, expressed for example as a concentration or as an absolute amount by weight or volume. Detection may also include both qualitative and quantitative aspects. Quantitative detection is typically, however, a more challenging pursuit than is a simple qualitative determination of presence or absence of a polynucleotide.

Detecting polynucleotides often involves the use of an enzyme. For example, some detection methods include polynucleotide amplification by polymerase chain reaction (PCR) or a related amplification technique. Other detection methods that do not amplify the polynucleotide to be detected also make use of enzymes. However, the functioning of enzymes used in such techniques may be inhibited by the presence of materials (known as inhibitors) that accompany the polynucleotide in many biological—particularly clinical—samples. The inhibitors may interfere with, for example, the efficiency and/or the specificity of the enzymes.

Polynucleotide detection today is moving towards ever more rapid, and ever more sensitive techniques. For example, rapid and accurate diagnosis of viral infections is invaluable for accurate patient management by directing the administration of appropriate antiviral therapy, eliminating the unnecessary utilization of antibiotics and monitoring individual response to the prescribed regimen. Given its significant advantages of sensitivity, specificity and time to result, polynucleotide detection (or nucleic acid testing) has become the presumptive international standard for viral diagnosis.

However, the application of nucleic acid testing to routine diagnosis of viral targets has been limited to large clinical reference labs and major hospital labs due to the high cost, complexity and skill level requirements for implementing such testing. While significant improvements have been made in recent years, the successful detection of RNA viruses in particular requires extremely laborious extraction procedures frequently relying on the use of toxic chemicals. Furthermore, RNA molecules can be very unstable and hence can require delicate processing/handling during their determination. These issues to date have been overcome with the use of large, expensive, time consuming robotic equipment.

With the current demands on practice of medicine, laboratories that carry out diagnostic testing on patient samples see substantial benefits from having extremely high throughput, which in itself is assisted if the time to arrive at a diagnostic outcome for a given sample is made as short as possible. Testing may also be made more rapid if the actual sample on which the tests are run is made as small as possible. More recently, there has been a growing need for a small, easy to use, low-cost, automated platform for the extraction of high quality RNA from viral targets in clinical specimens.

Correspondingly, then, the need to be able to isolate minute quantities of polynucleotides from complex biological samples in a manner that effectively avoids the presence of or reduces the detrimental impact of inhibitors is ever more important. Furthermore, given the availability of various stand-alone automated amplification apparatuses, it is desirable to be able to routinely and reliably extract from a raw clinical sample a quantity of polynucleotide that is ready—in team of purity and quantity—for amplification.

The discussion of the background herein is included to explain the context of the technology. This is not to be taken as an admission that any of the material referred to was published, known, or part of the common general knowledge as at the priority date of any of the claims found appended hereto.

Throughout the description and claims of the specification the word "comprise" and variations thereof, such as "comprising" and "comprises", is not intended to exclude other additives, components, integers or steps.

SUMMARY OF THE INVENTION

The process and materials herein are applicable to a number of testing targets, in particular those that are RNA based, such as Influenza (A & B), RSV, HSV, CMV, Adenovirus, and Enterovirus.

The technology herein provides excellent RNA—as well as DNA—capture and recovery via use of micro-particles having a high RNA and DNA binding capacity, such as 100 µg/mg beads, and a >90% release efficiency. In exemplary embodiments, 8-10 µg RNA can be extracted from an overnight culture. Processes, as described herein, permit very fast (15-20 minutes including lysis) RNA extraction from cellular or viral material, via a single tube process. Processes, as described herein, comprise a streamlined procedure having fewer steps (such as six) to proceed from raw sample to purified RNA. Such processes therefore provide an extremely effective clean-up of RNA from raw biological samples, thereby permitting PCR to be performed thereon. The methods and processes are applicable across a wide variety of sample matrices, as well as clinical buffers used when collecting raw samples, e.g., M4, UTM, and Todd Hewit Broth.

Suitable targets, that have assays used in clinical testing, and that may be the subject of sample preparation processes as described herein, include, but are not limited to: Chlamydia Trachomatis (CT); Neisseria Gonorrhea (GC); Group B Streptococcus; HSV; HSV Typing; CMV; Influenza A & B; MRSA; RSV; TB; Trichomonas; Adenovirus; Bordatella; BK; JC; HHV6; EBV; Enterovirus; and M. pneumoniae.

One aspect of the present invention relates to a method for processing one or more RNA and/or DNA compounds (e.g., to concentrate the RNA and/or DNA compound(s) and/or to separate the RNA and/or DNA compound(s) from inhibitor compounds (e.g., hemoglobin, peptides, faecal compounds, humic acids, mucousol compounds, DNA binding proteins, or a saccharide) that might inhibit detection and/or amplification of the RNA and/or DNA compounds).

In some embodiments, the method includes contacting the sample containing the RNA and/or DNA compounds and PAMAM (Generation 0) that preferentially associates with (e.g., retains) the RNA and/or DNA compounds as opposed to inhibitors. The PAMAM (Generation 0) is typically bound to a surface (e.g., a surface of one or more particles). The PAMAM (Generation 0) retains the RNA and/or DNA compounds so that the RNA and/or DNA compounds and inhibitors may be separated, such as by washing the surface with the compound and associated RNA and/or DNA compounds. Upon separation, the association between the RNA and/or DNA compound and the PAMAM (Generation 0) may be disrupted to release (e.g., separate) the RNA and/or DNA compounds from the compound and surface.

The present disclosure provides for a method for isolating polynucleotides from a cell-containing sample, the method comprising: contacting the sample with a lysis solution and a plurality of binding particles coated in PAMAM (Generation 0), so that the polynucleotides are liberated from the cells and become bound to the PAMAM (Generation 0), thereby creating binding particles bound with polynucleotides and a solution containing residual cellular matter; compacting the binding particles bound with polynucleotides; removing the solution containing residual cellular matter; washing the binding particles; and releasing the polynucleotides from the binding particles.

The present disclosure further includes a process for concentrating RNA from a sample containing polymerase chain reaction inhibitors, the method comprising: contacting between 500 µl and 1 ml of the sample with a plurality of RNA binding particles, the binding particles configured to preferentially retain the RNA in the sample as compared to the polymerase chain reaction inhibitors; concentrating the plurality of particles having the one or more polynucleotides bound thereto into an effective volume between 50 nanoliters and 5 microliters; and releasing the one or more polynucleotides into <30 µl of solution.

The present disclosure still further includes a composition comprising: carboxyl modified microparticles; and PAMAM (Generation 0) bound via one or more amine groups per molecule to one or more of the carboxylic acid groups on the microparticles.

The present disclosure additionally includes a kit, comprising: a number of sealed tubes, each containing lysis buffer; a tube containing lyophilized microparticles having PAMAM (Generation 0) bound thereto; a tube containing liquid wash reagents, sufficient to analyze the number of samples; and a tube containing liquid release reagents, sufficient to analyze the number of samples, wherein each component of the kit is stored in an air-tight container.

The present disclosure still further includes a kit, comprising: a first air-tight pouch enclosing a number of tubes, each tube containing lyophilized microparticles having PAMAM (Generation 0) bound thereto; a second air-tight pouch enclosing a number of reagent holders, each holder comprising: a tube containing liquid lysis reagents; a tube containing liquid wash reagents; and a tube containing liquid release reagents.

The present disclosure additionally includes a method of making a polynucleotide retention member, the method comprising: washing a quantity of microspheres with carbonate and MES buffer; preparing sulfo-NHS and EDAC; incubating the microspheres with sulfo-NHS and EDAC for 30 minutes; washing the microspheres with MES and borate buffer; contacting the microspheres with PAMAM(0) for 8-10 hours; and rinsing unbound PAMAM(0) from the microspheres.

BRIEF DESCRIPTION OF THE DRAWINGS

Like reference symbols in the various drawings indicate like elements.

DETAILED DESCRIPTION

Figure 1:
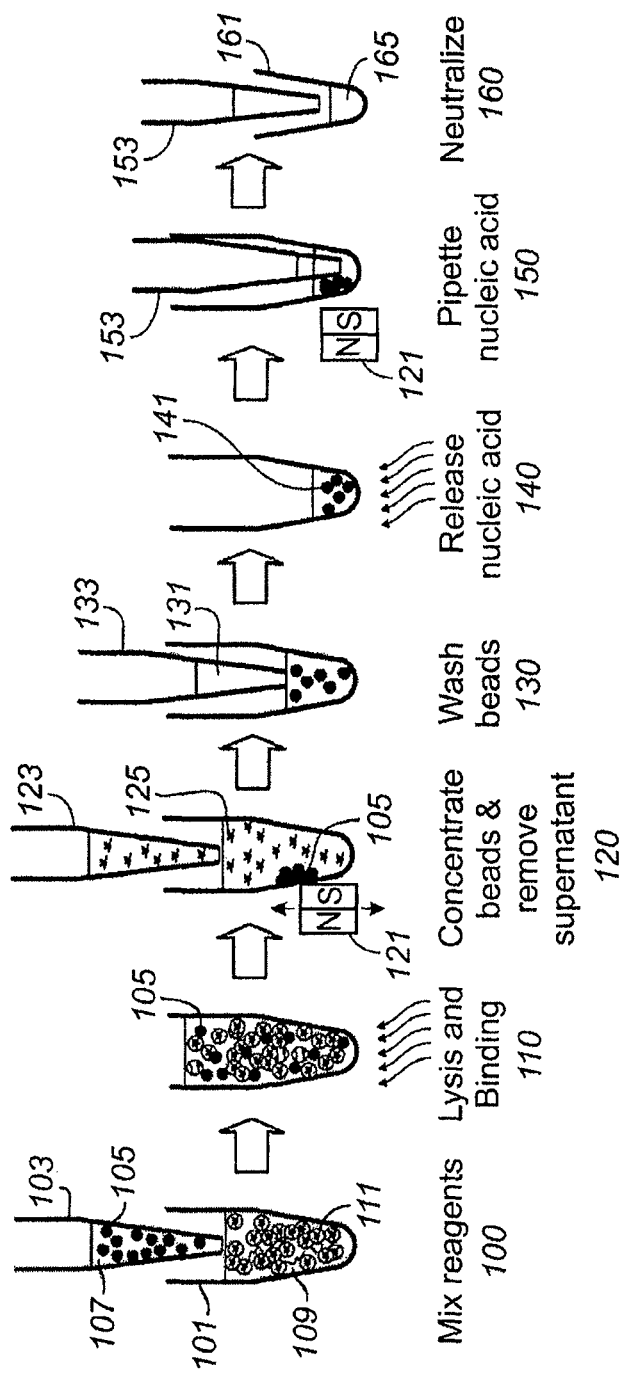
FIG. 1 shows schematically a typical process as described herein.

Analysis of biological samples often includes determining whether one or more polynucleotides (e.g., a DNA, RNA, mRNA, or rRNA) is present in the sample. The technology described herein has applicability to determining both RNA and DNA that is present in a sample. For example, a sample may be analyzed to determine whether the RNA of a particular pathogen is present, and also whether DNA of another or the same pathogen is present. If present, the RNA or the DNA may together or separately be indicative of a corresponding disease or condition.

Accordingly, the technology described herein is directed to materials that bind polynucleotides, and use of such materials in isolating polynucleotides, such as DNA and RNA, from biological samples. The materials, in conjunction with methods of using the materials, provide for rapid and reliable extraction of RNA and DNA from many different types of biological samples, including quantitative determination of both the RNA and the DNA. Such methods are typically referred to as "sample preparation" methods. What is meant by such a term is the liberation, extraction, concentration, and/or isolation, of RNA and/or DNA of a target organism from a raw sample—such as obtained directly from a patient or an agricultural or food product—where the raw sample contains the target RNA and/or target DNA bound in cellular form. The liberated target RNA and/or target DNA is placed, at the culmination of the process, in a form suitable for amplification and/or detection.

The terms DNA (deoxyribonucleic acid) and RNA (ribonucleic acid), and together as polynucleotides, as used herein can mean an individual molecule or population of molecules, such as identifiable by having a specific nucleotide sequence common to all, or can mean collectively molecules of DNA or RNA having different sequences from one another. For example, a biological sample from a human patient may contain DNA from the patient's cells, having one sequence, and DNA or RNA from cells of a pathogen, having a different sequence from that of the patient's DNA. The sample is thus referred to as containing DNA and RNA (or, together, polynucleotides), even though there are molecules of DNA (or RNA) in the sample that are different (chemically distinct) from one another. The methods herein can be used to liberate, collectively, molecules of DNA and RNA from both the patient's and the pathogen's cells in such a sample. Typically, however, in such an instance, it will usually be the DNA or RNA of the pathogen that will be of interest, and which will be selectively amplified from amongst all the DNA and RNA that is ultimately isolated from the sample. The DNA and RNA that is best suited for extraction by the methods herein has a size less than 7.5 Mbp, though it would be understood that larger DNA and RNA molecules may be susceptible to extraction and detection by the methods herein.

Typically, biological samples are complex mixtures. For example, a sample may be provided as a blood sample, a tissue sample (e.g., a swab of, for example, nasal, buccal, anal, or vaginal tissue), a biopsy aspirate, a lysate, as fungi, or as bacteria. The RNA and/or DNA to be determined is normally contained within particles (e.g., cells such as white blood cells, or red blood cells), tissue fragments, bacteria (e.g., gram positive bacteria, or gram negative bacteria), fungi, or spores. One or more liquids (e.g., water, a buffer, blood, blood plasma, saliva, urine, cerebral spinal fluid (CSF), or organic solvent) is typically part of the sample and/or is added to the sample during a processing step. The materials and methods described herein are compatible with a variety of clinical matrices, at least including blood, urine, CSF, swab, and plasma.

Methods for analyzing biological samples include releasing RNA and/or DNA from the particles (e.g., bacteria) in the sample, amplifying one or more of the released RNA and/or DNA (e.g., by polymerase chain reaction (PCR)), and determining the presence (or absence) of the amplified polynucleotide(s) (e.g., by fluorescence detection).

Clinical samples present a variety of challenges especially in the detection of target RNA and DNA through PCR or similar technologies. A target nucleic acid could be present in a concentration as low as 10 copies per milliliter as measured against a background of millions or billions of copies of competing nucleic acids (such as from a patient's normal cells). Moreover, a variety of other biochemical entities present in the clinical sample inhibit PCR. The inhibitors may also frustrate isolation of RNA or DNA from the sample, such as by being captured by a material designed to retain the RNA or DNA. If the concentration of inhibitors is not reduced relative to the RNA or DNA to be determined, the analysis can produce false negative results. Examples of these inhibitors, dependent upon the biological sample in question, are cellular debris such as membrane fragments, humic acids, mucousal compounds, hemoglobin, other proteins such as DNA binding proteins, salts, DNAases, fecal matter, meconium, urea, amniotic fluid, blood, lipids, saccharides, and polysaccharides. For example, such inhibitors can reduce the amplification efficiency of DNA and RNA by PCR and other enzymatic techniques for determining the presence of DNA and RNA.

Therefore, an effective sample preparation method should lead to a concentration of the target RNA or DNA, and should minimize presence of inhibitory substances. The methods described herein may increase the concentration of the DNA and/or RNA to be determined and/or reduce the concentration of inhibitors relative to the concentration of DNA and/or RNA to be determined.

In addition, cells of some target organisms, such as gram positive bacteria (e.g. Group B Strep), are very hard to lyse, meaning that lysing conditions can be very severe. Such organisms may require additional chemicals for lysing, such as mutanolysin, and may also require higher temperatures for optimal lysis. Such conditions may be accommodated by the materials and methods described herein.

Sample Preparation Process

A typical sample preparation process may be carried out in a processing chamber that includes a plurality of particles (e.g., beads, microspheres) configured to retain RNA and/or DNA of the sample under a first set of conditions (e.g., a first temperature and/or first pH) and to release the RNA under a second set of conditions (e.g., a second, higher temperature and/or a second, more basic, pH), and to release DNA under a third set of conditions (e.g., a third, different temperature and/or a third, more basic, pH than that used in the first and second conditions). Typically, the DNA and RNA are retained preferentially as compared to inhibitors that may be present in the sample.

An exemplary sample preparation process is illustrated in FIG. 1. The various reagents referred to in connection with FIG. 1 are described in further detail elsewhere herein. At 100, a process tube 101, such as a standard laboratory 1.7 ml microcentrifuge tube, contains a biological sample comprising a liquid 109, such as an aqueous solution, and cellular materials 111, wherein at least some of the cellular materials may contain RNA and/or DNA of a target of interest. The biological sample may be any of those described elsewhere herein, and process tube 101 may be any tube or suitable vessel, as further described herein. It is to be understood that, although the process is illustrated with respect to FIG. 1, the process is not limited to be carried out in a tube. The sample and various reagents may be, for example, delivered to, and mixed and reacted within, chambers of a microfluidic device such as a microfluidic cartridge, as further described in U.S. patent application Ser. No. 11/281,247, filed Nov. 16, 2005 and incorporated herein by reference.

A first pipette tip 103 contains a solution 107 of microparticles 105, that are delivered to the process tube and contacted with the biological sample contained therein. The surfaces of particles 105 are modified to have PAMAM(0) attached, as further described herein, so that they retain RNA and/or DNA in preference to inhibitors in solution. Solution 107 may be a lysis solution, as further described herein. The lysis solution may contain a detergent, in addition to various enzymes, as described elsewhere herein. Thorough mixing of the microparticles, the solution, and the biological sample may occur simply by turbulent combination of the two solutions upon release of the microparticle containing solution from the pipette tip, or may occur via mechanical or manual agitation of process tube 101.

First pipette tip 103 is positioned above process chamber 101, such as by manual operation by a user, or such as by an automated pipetting head, an example of which is described in U.S. provisional patent application Ser. No. 60/959,437, filed Jul. 13, 2007, which is incorporated herein by reference.

At 110, using the same process tube 101, the microparticles, biological sample, and lysis reagents are incubated, such as by applying heat from an external source, as shown, so that the cells in the biological sample are lysed, and liberate RNA and/or DNA. Under these conditions, the DNA molecules bind to suitably configured surfaces of the microparticles, as further described herein. Typically, the particles retain RNA and/or DNA from liquids having a pH about 9.5 or less (e.g., about 9.0 or less, about 8.75 or less, about 8.5 or less). It is to be noted that the binding of DNA to the affinity microparticles happens concurrently with the lysis process, and the binding is not adversely affected by the presence of detergents and, in some instances, lytic enzymes in the lysis solution. The choice of temperature is dictated by what is required to lyse the cells in question, and heat is not required to effectuate binding of the RNA or DNA to the particles. Typically, those cells having tougher cell walls (e.g., lysteria, or anthrax) will require higher temperatures. For example, Chlamydia determination utilizes a temperature of 37° C. for a duration of 5-10 minutes for lysis and binding, whereas Group B Streptococcus determination utilizes a temperature of 60° C. for a duration of 5-10 minutes. Generally, the liquid is heated to a temperature insufficient to boil liquid in the presence of the particles.

At 120, the microparticles are concentrated or compacted, and the remaining solution containing residual cellular matter 125 is removed, for example by a second pipette tip 123. By compacted is meant that the microparticles, instead of being effectively uniformly distributed through a solution, are brought together at a single location in the process tube, in contact with one another. Where the microparticles are magnetic, compaction of the microparticles may be achieved by, for example, bringing a magnet 121 into close proximity to the outside of the process chamber 101, and moving the magnet up and down outside the chamber. The magnetic particles are attracted to the magnet and are drawn towards the inside of the wall of the process chamber adjacent the magnet.

Pipette tip 123 removes as much of the remaining solution (sometimes referred to as supernatant, or solution having residual cellular matter) as is practical without drawing up significant quantities of microparticles. Typically a pipette tip may slide into process chamber 105 without contacting the microparticles. In this way the microparticles are concentrated, by being present in a smaller volume of solution than hitherto. Pipette tip 123 may be a different tip from pipette tip 103, or may be the same tip. In some embodiments, after removal of the solution containing residual cellular matter, less than 10 microliters of solution is left along with the particles. Typically this is achieved by both compaction of the microparticles to a small pellet, but also positioning that pellet away from the location wherein the pipette will be introduced for removal of the supernatant. The positioning of the pipette in relation to the bottom of the tube is also important so that almost all of the supernatant is removed. The pipette tip should be almost close to the bottom of the tube (within 1-2 mm) but without completely sealing the pipette tip against the tube bottom. A stellated pattern may also be used at the bottom of the lysis tube, (as described in U.S. provisional patent application Ser. No. 60/959,437, filed Jul. 13, 2007, and incorporated herein by reference), but the positioning of the patterns in relation to the location of the magnet becomes important so that the sliding of the compacted microparticles is not hindered and the crevices between vertices of the stellated pattern do not trap microparticles.

At 130, a third pipette tip 133 delivers a wash solution 131 to the process chamber 101 containing compacted microparticles. The wash solution may comprise, e.g., a buffer such as Tris-EDTA with a surfactant such as 1% Triton X 100, and having an overall pH 8.0. Typically, the volume of wash buffer is 100 microliters or less, where the sample is 2 ml or less in volume. The wash solution is used to wash off any non-DNA and non-RNA molecules, such as inhibitors, that may have become bound to the microparticles. The wash solution is chosen to preferentially wash off non-RNA and non-DNA molecules while leaving in place those RNA and/or DNA molecules bound to the microparticles. Pipette tip 133 may be a different tip from either or both of pipette tips 103 and 123, or may be one of those tips being re-used.

In order to release the RNA and, separately, the DNA from the particles, the wash solution 131 is replaced with an alkaline (pH ~9.0) release solution, e.g., a buffer solution having a pH different from that of the wash solution. This can be done by pipetting out as much of the wash solution as possible, for example, having a residual volume <5 microliters, and then dispensing release buffer with a new pipette tip. In case the same tip is used, the liquid should be completely drained off so as not to dilute the release solution. For example, at 140, a release solution 141 is delivered to process chamber 101 so that the RNA bound to the micro-particles can be liberated from those micro-particles. In general, the PAMAM (Generation 0) on the particles (as further described herein) most efficiently releases RNA when the pH is about 9. Consequently, RNA can be released from the particles into the surrounding liquid. In some instances, heat may be applied to the process tube, such as to heat the solution to 85° C., to facilitate release of the RNA. Generally, the liquid is heated to a temperature insufficient to boil liquid in the presence of the particles. In some embodiments, the temperature is 100° C. or less (e.g., less than 100° C., about 97° C. or less). In some embodiments, the temperature is about 65° C. or more (e.g., about 75° C. or more, about 80° C. or more, about 90° C. or more). In some embodiments, the temperature is maintained for about 1 minute or more (e.g., about 2 minutes or more, about 5 minutes or more, about 10 minutes or more). In some embodiments, the temperature is maintained for about 30 minutes (e.g., about 15 minutes or less, about 10 minutes or less, about 5 minutes or less). In some embodiments, the process tube is heated to between about 65 and 90° C. (e.g., to about 70° C.) for between about 1 and 7 minutes (e.g., for about 2 minutes). In other embodiments, the heating is to 85° C. for 3 minutes. In still other embodiments, the heating is to 65° C. for 6 minutes. In general, a longer heating time is required for a lower temperature. Alternatively, or in combination, particles with retained RNA are heated to release the RNA without assistance of a release solution. When heat alone is used to release the RNA, the release solution may be identical with the wash solution.

Typically, the RNA from a 2 ml sample, and according to the description of the lysis, binding, and washing described elsewhere therein, is released into about 20 microliters or less (e.g., about 10 microliters or less, about 5 microliters or less, or about 2.5 microliters or less) of liquid.

While releasing the RNA has been described as including heating, the RNA may be released without heating. For example, in some embodiments, the release solution has an ionic strength, pH, surfactant concentration, composition, or combination thereof that releases the RNA from the retention member without requiring heat.

It is to be noted that excessive shearing, such as is caused by rapid movements of the liquid during suck-and-dispense mixing operations during wash and release (typically during DNA release) in the sample preparation process may release PAMAM (Generation 0) from the surface of the particles, which itself causes downstream inhibition of PCR. The mixing steps should be limited to less than 10 suck-and-dispense operations, where the amount moved back and forth ranges from 1-20 microliters moved in the pipette, performed over 1-10 seconds per suck-and-dispense operations.

At 150 the microparticles, now having essentially no RNA bound thereto, can be compacted or concentrated in a similar manner to that described for 120, but in this case to facilitate removal of the release solution containing the RNA dissolved therein. For example, magnetic beads can be collected together on the interior of the process chamber wall by bringing magnet 121 into close proximity to the outside of the process chamber. In FIG. 1, magnet 121 is used to compact the microparticles at both stages 120 and 150, though it would be understood that a different magnet could be used in both instances.

In instances where a sample contains both RNA and DNA, and it is desired to determine both a particular RNA and a particular DNA, the procedures at 140 and 150, as described herein, may be repeated, using a second release solution that is designed to release DNA. As described further in U.S. patent application Ser. No. 12/172,208, filed on even date herewith, and entitled "POLYNUCLEOTIDE CAPTURE MATERIALS, AND METHODS OF USING SAME", a solution designed to release DNA typically has a pH of about 12 or greater. Such a procedure relies on the fact that RNA and DNA have different pKa's and therefore will elute from the surface of a particle to which they are non-covalently bound, at different pH's from one another. Similar considerations, such as release conditions (temperature, reagent concentrations, etc.) apply to release of DNA as to RNA.

It is to be noted that, thus far, all of the processing steps have taken place in a single tube. This is advantageous for a number of reasons: first, that unnecessary liquid transfer steps will necessarily lead to some loss of target material. Additional liquid transfer steps will also add to the overall time of the protocol. It should be noted that performing all the liquid processing in a single tube is not an easy task primarily because of the residual volumes left between successive liquid transfers. It becomes even more difficult when the final elution volume is very low, such as less than 30 microliters, or less than 20 microliters or less than 10 microliters, or less than 5 microliters. Nevertheless, with the protocols described herein, very good yields may be obtained.

The RNA, and/or subsequently the DNA, liberated from the microparticles can each be drawn up into a fourth pipette tip 153 in solution in the release solution. Pipette tip 153 need not be different from all of pipette tips 103, 123, and 133 and may therefore represent a re-use of one of those tips. Although it is desirable to use magnetic beads, non-magnetic beads may also be used herein, and separated by, e.g., centrifugation, rather than by use of a magnet.

In certain embodiments, the ratio of the volume of original sample introduced into the processing tube to the volume of liquid into which the RNA or DNA is released is at least about 10 (e.g., at least about 50, at least about 100, at least about 250, at least about 500, at least about 1,000). In some embodiments, RNA or DNA from a sample having a volume of about 2 ml can be retained within the processing tube, and released, after binding and washing, into about 4 microliters or less (e.g., about 3 microliters or less, about 2 microliters or less, about 1 microliter or less) of liquid.

In some embodiments, the sample has a volume larger than the concentrated volume of the binding particles having the RNA or DNA bound thereto by a factor of at least about 10.

In other embodiments, the sample has a volume of 100 µl-1 ml, and the compacted particles occupy an effective volume of less than 2 microliters.

The liquid into which the RNA or DNA is released typically includes at least about 50% (e.g., at least about 75%, at least about 85%, at least about 90%, or at least about 95%) of the RNA or DNA respectively present in the sample 109. Thus, for example, ~8-10 µg DNA can be liberated from 1 ml of overnight culture, and 2-4 µg DNA can be extracted from one buccal swab. The concentration of RNA or DNA present in the release liquid may be higher than the respective concentration in the original sample because the volume of release liquid is typically less than the volume of the original liquid sample. For example, the concentration of DNA in the release liquid may be at least about 10 times greater (e.g., at least about 25 times greater, at least about 100 times greater) than the concentration of DNA in the sample 109. The concentration of inhibitors present in the liquid into which the RNA or DNA is released is generally less than the concentration of inhibitors in the original fluidic sample by an amount sufficient to increase the amplification efficiency for the RNA or DNA over that which could be obtained from an unpurified sample.

In general, although the processes and materials described herein are capable of performing well—usually with only routine adaptation—over a wide range of sample sizes, and reagent volumes, for most practical applications (considering the size of most biological samples subject to diagnostic analysis), the volume of compacted particles having RNA and/or DNA bound thereto that results (prior to release) is in the range 2-3 µl, and is independent of the sample volume, up to about 2 ml of sample. Typically the quantity of microparticles required is determined by the quantity of RNA and/or DNA in the sample. It is found that, given the efficiency of binding to the particles, 0.5 mg of particles is sufficient for most manual applications, and most involving automated pipetting, regardless of sample size. Thus, for example, for samples having volumes from 0.5 microliters to 3 milliliters, the volume of the compacted particles is 2-3 µl. For example, for Chlamydia, the sample size is typically 1 ml, and 0.5 mg of particles is sufficient. For other applications, DNA from a 2 ml sample can also be extracted with 0.5 mg particles, or in some instances 1 mg beads can be used. For smaller samples, such as having a volume of 5 µl, it is still typical to use only 0.5 mg particles.

In order to agitate the solution at various stages during the manual process, the solution may be pipetted up and down a number of times, such as 10 times, 15 times, or 20 times. Such a procedure is acceptable during the release step as well as the wash steps. Vortexing also works for these steps. However, for the automated process, cannot tolerate any mix steps, the number of mixing operations is kept at a minimum as this was possibly causing some PAMAM(0) to come off and inhibit downstream PCR.

The process described herein represents an extremely effective clean-up of a sample in preparation for PCR and provides the capability to detect as few as 25 copies of RNA or DNA from 1 milliliter of clinical sample. The RNA or DNA is present in a high level of concentration because the elution volume can be as low as 3 microliters. There is also a low residual sample liquid and/or wash volume in the concentrated microspheres, thereby minimizing dilution by sample or wash buffer, as well as minimizing inhibition from residual sample.

The time interval between introducing the polynucleotide containing sample to processing tube 101, and releasing the RNA or DNA into the release liquid is usually between 10 and 30 minutes, and is typically about 15-20 minutes, or may be 15 minutes or less (e.g., about 10 minutes or less, about 5 minutes or less). These times include the lysis time (which doubles up as a sample-binding time), and are extremely fast. To release both RNA and DNA, separately, from a single sample, it is only necessary to add an additional release procedure, as in 140 in FIG. 1.

Optionally, at 160 in FIG. 1, the released RNA or DNA in solution may be neutralized by contacting it with a neutralization solution 165 (e.g., an equal volume of 25-50 mM Tris-HCl buffer pH 8.0). For example, the RNA or DNA in solution in pipette tip 153 may be released into a second process chamber, or vessel, 161 such as a standard laboratory PCR tube, in which the neutralization solution is present. The PCR tube may be removed and introduced into a PCR machine for further analysis. Typically, the solutions for extracting RNA are close enough to neutrality that a separate neutralization step is not required.

The RNA or DNA in solution in vessel 161 is in a state that it can be amplified, such as by PCR, and detected. Furthermore, the foregoing process steps are extremely reliable and robust, and enable quantitative assays of the extracted RNA or DNA over 7 log dilutions (10-$10^7$ copies of target RNA or DNA/ml of sample).

The process of FIG. 1 has demonstrated effectiveness in manual as well as automated formats.

The process shown in FIG. 1 may be carried out in conjunction with a reagent holder, in which the process chamber may be situated, and in which are found appropriate quantities of microparticles, lysis solution, wash solution, release solution, and neutralization solution, each of which is accessible to one or more pipette tips and for use as shown in FIG. 1. An exemplary reagent holder is described in U.S. provisional patent application Ser. No. 60/959,437, filed Jul. 13, 2007, and incorporated by reference herein.

Where a magnet is shown in FIG. 1 for use in compacting magnetic microparticles, a magnetic separator, as described in U.S. provisional patent application Ser. No. 60/959,437, filed Jul. 13, 2007, and incorporated by reference herein, may be used.

Where it is shown in FIG. 1 that heat may be applied to process chamber 101, a heater assembly, as described in U.S. provisional patent application Ser. No. 60/959,437, filed Jul. 13, 2007, and incorporated by reference herein, may be used.

The process shown in FIG. 1 is optimally used to prepare highly pure and concentrated RNA or DNA for use in low-volume (e.g. 4 μl) PCR reactions, such as may be carried out in a microfluidic cartridge, for example a microfluidic cartridge described in U.S. provisional patent application Ser. No. 60/959,437, filed Jul. 13, 2007, and incorporated herein by reference.

Figure 2:
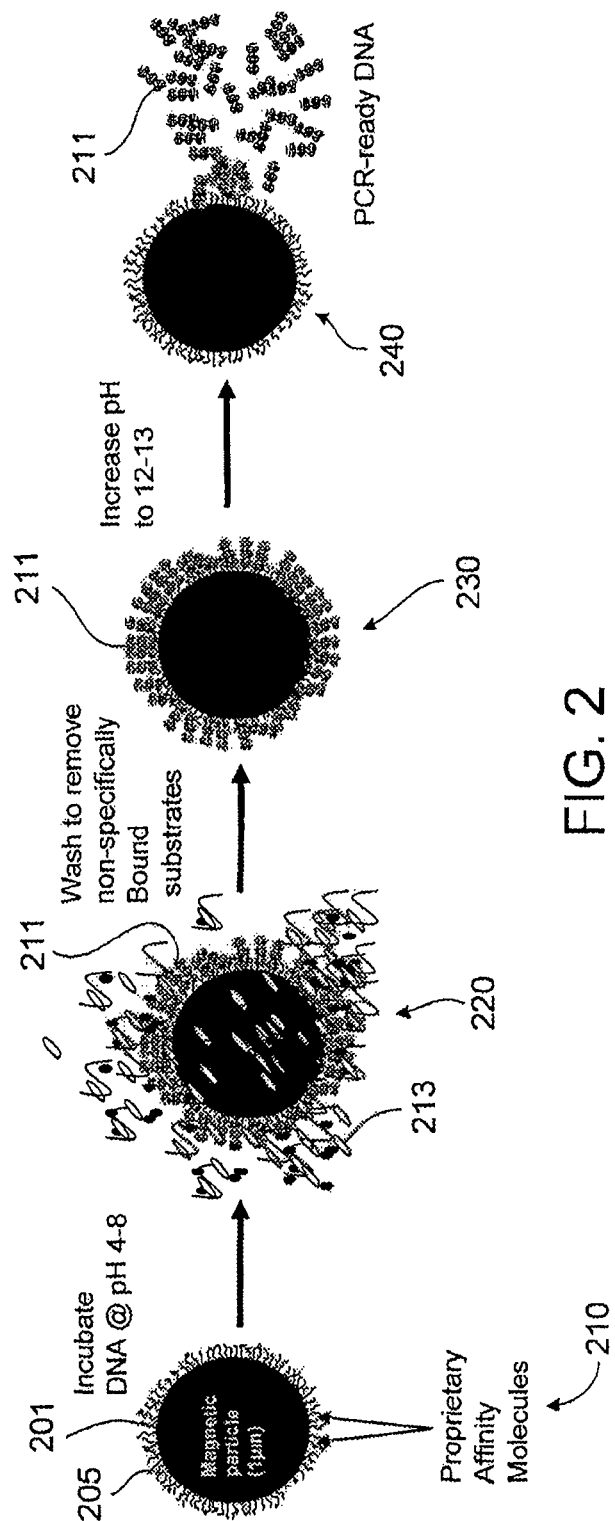
FIG. 2 shows schematically the action of DNA affinity beads as further described herein.

FIG. 2 shows, schematically, a sample preparation process at the molecular level. At 210, a typical magnetic particle 201, having a diameter of 1 μm, is shown. Attached to the surface of particle 201 are molecules 205 having a binding affinity for polynucleotides in solution surrounding the particle. Attachment of molecules 205 is usually via covalent bonds. Such molecules are further described herein and in some embodiments are molecules of PAMAM (Generation 0). From 210 to 220, the magnetic particle is incubated in a solution containing RNA and/or DNA, at a pH of 4-8, lower than the pKa of molecules 205. At 220, particle 201 is shown having polynucleotide (i.e., DNA and/or RNA) molecules 211 attached to the affinity molecules 205. Also shown are various other non-specifically bound substrates 213, denoted by small ovals, cigar-shapes, and curved lines.

Moving from 220 to 230 in FIG. 2, the particle 201, to which is bound both RNA and/or DNA molecules 211, and non-specifically bound molecules 213, is washed to remove the non-specifically bound substrates, leaving a particle coated in affinity molecules 205 and RNA and/or DNA molecules 211 bound thereto. From 230 to 240, the RNA and/or DNA molecules 211 are released from the surface of the particle by increasing the pH of the solution surrounding the particle to a pH of 9 (RNA) and, subsequently a pH of 12-13 (to release DNA). The released RNA and/or DNA molecules can be separately collected in a PCR-ready format.

While samples and various solutions have been described herein as having microliter scale volumes, other volumes can be used. For example, processing tubes with surfaces (e.g., particles) configured to preferentially retain RNA and/or DNA as opposed to inhibitors may have large volumes (e.g., many tens of microliters or more, at least about 1 milliliter or more). In some embodiments, the processing tube has a bench-top scale, and other solutions are correspondingly scaled up.

Polynucleotide Capture Material

Suitable polynucleotide affinity molecules are those that offer a very high density of positively ionizable charges at a low pH, and enable strong attraction and binding of polynucleotides, including RNA and DNA from a clinical lysate, within a few minutes.

A typical embodiment of the materials herein uses: Polyamidoamine (PAMAM) Generation 0, available from the Sigma-Aldrich Chemical Company ("Sigma-Aldrich"), product number 412368. This material, referred to hereinafter as "PAMAM (Generation 0)" or "PAMAM(0)" of "PAMAM (G0)", is a dendrimer whose molecules have the following structure.

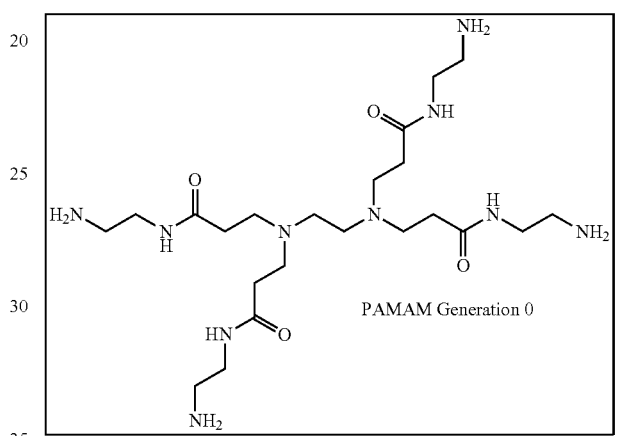

The core of the molecule is an ethylene diamine substituted twice on both nitrogen atoms by an acetyl group. Each acetyl group has itself reacted with ethylene diamine monomers to yield amino-substituted amide groups.

The form of PAMAM(0) suitable for use herein is not limited to that product available from Sigma-Aldrich, however. PAMAM(0), being dendrimeric in nature, admits of a wide range of forms, controlled at least in part by the extent of dendrimerization permitted during its synthesis. Thus, many variants of PAMAM(0), having variously, different numbers of substituting units, are suitable for use herein. In general, there is a range of sizes of dendrimer molecule (or PAMAM (0) derivative) that is suitable for polynucleotide capture: smaller sizes don't capture enough RNA or DNA, whereas larger sizes retain the RNA or DNA too strongly, and do not permit easy release. Additionally, different monomers from ethylene diamine may be used to make a variant of PAMAM suitable for use herein. Such monomers may include, without limitation, 1,2-propylene diamine, 1,3-propylene diamine, 1,2-butylene diamine, 1,3-butylene diamine, and 1,4-butylenediamine.

Molecules of PAMAM suitable for use herein may also be characterized by molecular weight. In particular, PAMAM(0) has a molecular weight of 516; other suitable PAMAM molecules have weights in the range 500-600 Da.

PAMAM(0) can itself function as an inhibitor of enzymatic processes such as DNA and RNA amplification, and therefore it is important that it be used in a manner in which it does not reside in solution together with the released RNA and/or DNA. Aspects of this are further described in the Examples, hereinbelow.

Support Materials

During use, PAMAM(0) is typically immobilized on, such as bound to the surface of, a solid support such as carboxylated beads, or magnetic or non-magnetic beads. In many embodiments, such a solid support comprises microparticles, such as beads, and microspheres. These terms, microparticles, beads, and microspheres may be used interchangeably herein. The particles are typically formed of a material to which the PAMAM(0) can be easily associated. Exemplary materials from which such particles can be formed include polymeric materials that can be modified to attach a ligand. Typically, such a solid support itself may be derivatized to yield surface functional groups that react easily with PAMAM(0) molecules to create a chemical bond between the surface and the PAMAM(0). A frequently-employed—and desirable—surface functional group is the carboxylic acid (COOH) group. Exemplary polymeric materials that provide, or can be modified to provide, carboxylic groups and/or amino groups available to attach PAMAM(0) include, for example, polystyrene, latex polymers (e.g., polycarboxylate coated latex), polyacrylamide, polyethylene oxide, and derivatives thereof. Polymeric materials that can used to form suitable particles are described in U.S. Pat. No. 6,235,313 to Mathiowitz et al., which patent is incorporated herein by reference. Other materials include glass, silica, agarose, and amino-propyl-tri-ethoxy-silane (APES) modified materials.

During the process of reaction of a PAMAM(0) molecule with a carboxylated particle, such as a magnetic particle, one of the amine groups out of the total possible amine groups on a PAMAM(0) molecule, such as 6 possible groups in the aforementioned product from Sigma Aldrich, is consumed to react with the COOH group of the surface of the particle to form a carbodiimide bond. (See, e.g., U.S. application Ser. No. 11/281,247, page 40). The remainder of the total number amine groups, such as 5 groups in the aforementioned product from Sigma Aldrich, are available for protonation.

In some embodiments, a synthetic protocol comprises: washing a quantity of microspheres with carbonate and MES buffer; preparing sulfo-NHS and EDAC; incubating the microspheres with sulfo-NHS and EDAC for 30 minutes; washing the microspheres with MES and borate buffer; contacting the microspheres with PAMAM(0) for 8-10 hours; and rinsing unbound PAMAM(0) from the microspheres. An example of synthetic protocols for making PAMAM(0)-bound microparticles, is given in the Examples, hereinbelow.

There are a variety of sources of bead or particle that can be used to bind PAMAM(0), and used in the processes described herein, for example: Seradyn Magnetic carboxyl modified magnetic beads (Part #3008050250, Seradyn), Polysciences BioMag carboxyl beads, Dynal polymer encapsulated magnetic beads with a carboxyl coating, and Polybead carboxylate modified microspheres available from Polyscience, catalog no. 09850.

The high density of the PAMAM(0) molecules on bead surfaces permits even a small quantity of beads (0.5 mg) to be used for clinical samples as large as a milliliter, and permits binding of even low levels of target RNA or DNA (<100 copies) in a background of billions of copies of other polynucleotides.

In some embodiments, at least some (e.g., all) of the particles are magnetic. In alternative embodiments, few (e.g., none) of the particles are magnetic. Magnetic particles are advantageous because centrifugation is generally not required to separate them from a solution in which they are suspended.

Particles typically have an average diameter of about 20 microns or less (e.g., about 15 microns or less, about 10 microns or less). In some embodiments, particles have an average diameter of at least about 4 microns (e.g., at least about 6 microns, at least about 8 microns). Magnetic particles, as used herein, typically have an average diameter of between about 0.5 microns and about 3 microns. Non-magnetic particles, as used herein, typically have an average diameter of between about 0.5 microns and about 10 microns.

The particle density is typically at least about $10^7$ particles per milliliter (e.g., about $10^8$ or about $10^9$ particles per milliliter). For example, a processing region, such as present in a microfluidic device configured for used in sample preparation, with a total volume of about 1 microliter, may include about $10^3$ beads.

In some embodiments, at least some (e.g., all) the particles are solid. In some embodiments, at least some (e.g., all) the particles are porous (e.g., the particles may have channels extending at least partially within them).

The microparticles described herein are not only suitable for use in process tubes that are handled by manual pipetting operations, but they can be used in a microfluidic devices, such as in sample concentrator, thereby enabling even sub-microliter elution volumes to be processed, as applicable.

The microparticles having PAMAM(0) bound thereto are particularly effective at capturing, and releasing RNA, and also DNA. In some embodiments, the ratio by weight of the RNA captured by the binding particles, to the binding particles prior to contact with the RNA, is 5-20%. In other embodiments, the ratio is 7-12%. In still other embodiments, the ratio is about 10%, corresponding to, e.g., 100 µg of RNA for each mg of particles.

The microparticles having PAMAM(0) bound thereto are particularly effective at capturing RNA, and/or DNA, consistently over a wide range of concentrations, thereby permitting quantitative analysis of the RNA and/or DNA to be carried out. In some embodiments, the binding particles capture 90% or more of the RNA or DNA liberated from cells into a solution in contact with the binding particles, over a range of 1 to $10^7$ copies of target RNA or DNA/milliliter of sample.

In some embodiments, the binding particles release 90% or more of the DNA bound thereto when certain release conditions are deployed.

Sample Preparation Kits

Microparticles, coated with PAMAM(0), can be provided to a user in solid form, such as in lyophilized form, or in solution. It is desirable that the reagent, however provided, can be used immediately by a user for whatever intended purpose, without any preparatory steps. Microparticles prepared by the methods described herein can be lyophilized by methods known in the art, and applicable to microparticles of the sizes and characteristics described herein.

In each of the kits described herein, neutralization reagents are not required in the event that the kits are only to be used for determining RNA compounds. Thus neutralization reagents may be provided but are optional. Neutralization reagents are typically deployed in instances when the kits are used for DNA determination or for determining both RNA and DNA.

Such microparticles can also be provided in kit form, in conjunction with other reagents that are used, for example, in sample preparation. One embodiment of a kit comprises a number of, such as 24, sealed tubes, each containing lysis buffer; a tube containing lyophilized microparticles having PAMAM(0) bound thereto; a tube containing liquid wash reagents, sufficient to analyze the number of samples; a tube containing liquid neutralization reagents, sufficient to analyze the number of samples; and a tube containing liquid release reagents, sufficient to analyze the number of samples, wherein each component of the kit is stored in an air-tight container. Other numbers of tubes available in kit form include 12, 25, 30, 36, 48, 50, 60, and 100. Still other numbers are also permissible and consistent with the description herein.

Furthermore, in other embodiments of such a kit, the tube containing lyophilized microparticles can additionally contain particles of reagents selected from the group consisting of: proteinase-k; proteinase-k and mutanolysin; and proteinase-k, mutanolysin, and an internal control DNA. The additional enzymes are often used in cell-specific lysis applications.

In other embodiments, a kit comprises: a first air-tight pouch enclosing a number of—such as 24—tubes, each tube containing lyophilized microparticles having PAMAM(0) bound thereto; a second air-tight pouch enclosing a number of reagent holders, each holder comprising: a tube containing liquid lysis reagents; a tube containing liquid wash reagents; a tube containing liquid neutralization reagents; and a tube containing liquid release reagents. Other numbers of tubes available in kit form include 12, 25, 30, 36, 48, 50, 60, and 100. Still other numbers are also permissible and consistent with the description herein.

Furthermore, in other embodiments of such a kit, the tube containing lyophilized microparticles can additionally contain particles of reagents selected from the group consisting of: proteinase-k; proteinase-k and mutanolysin; and proteinase-k, mutanolysin, and an internal control DNA. The additional enzymes are often used in cell-specific lysis applications.

Conditions of DNA Binding and Elution

One factor to consider when assessing the efficacy of a DNA-capture material is the material's pKa. The pKa of an acid, HA, is an equilibrium constant for the equilibrium

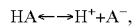

given by $pKa=-\log_{10} Ka$, where $Ka=[H^+][A^-]/[HA]$. It can be shown that, when the pH ($=-\log_{10} [H^+]$) of the solution is numerically equal to the pKa of the acid, the acid is 50% dissociated at equilibrium. Therefore, knowing the pKa of a material gives an indication of the pH, below which it is largely dissociated (in anion form), and above which it is largely unionized.

The pKa for an amino group is defined for its conjugate base, as follows: a protonated amine, $R-NH_3^+$ is in dissociative equilibrium:

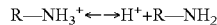

and its pKa is given by $-\log_{10} Ka$, where $Ka=[H^+][R-NH_2]/[R-NH_3^+]$.

Because a nitrogen atom is trivalent, and due to the conditions of dendrimerization, each molecule of PAMAM(0) has a mixture of primary, tertiary amine groups. Therefore, PAMAM(0) molecules exhibit multiple pK's over a range of values roughly consonant with the range of pKa's spanned by primary, and tertiary aliphatic amines, whose pKa's typically lie in the range 10-11, as evidenced by, for example, Table 12.2 of *Organic Chemistry*, 2$^{nd}$ Ed., Allinger, et al., Eds., Worth Publishers, Inc. (1976). However, according to information provided by the manufacturer of PAMAM(0), Dendritech of Midland, Mich., PAMAM is in fact likely to have pKa's in the range of 5.5 (for the tertiary amines in the interior of the molecule)-9.5 (for the primary amines on the surface of the PAMAM molecules). A journal article that references this data is Tomalia, et al., Angew. Chem. Int. Ed. Engl., 29, 138-175 (1990), at page 163, right-hand column.

PAMAM(0) is effective as a binder for DNA in the processes described herein at least in part because the amine groups of the PAMAM(0) have a pKa of between 5-9. Thus, at low pH it is typically positively charged—and may even carry multiple positive charges per molecule arising from protonations of the amine groups at pH's lower than its pKa—and is therefore able to bind strongly to polynucleotides such as DNA and RNA, which typically comprise polyanions (are predominantly negatively charged) in solution.

During the use of the PAMAM(0) molecule in the processes described herein, the pH of the binding buffer (typically TRIS) used to lyse cells at the same time as binding liberated DNA to the particles, is approximately 7-8. At this pH, all the amines (6 possible groups per PEI molecule, as available from Sigma) remain protonated (positively charged) and hence strongly attract negative charged DNA molecules to bind towards the beads.

PAMAM(0) molecules are also advantageous because they are resistant to, e.g., are immune to, degradation by lytic enzymes, protease enzymes (e.g., mixtures of endo- and exo-proteases such as pronase that cleave peptide bonds), harsh chemicals such as detergents, and heat up to 95° C., and as such are able to bind RNA and DNA during the lysis process as well. Thus, cell lysis and RNA and/or DNA binding can be combined into a single (synchronous) step, thereby both saving time and at least one processing step. The strong binding of RNA and/or DNA molecules to PAMAM(0) enables rapid washing of affinity beads coated in PAMAM(0) to remove PCR inhibitors using a wash solution. The release of RNA and/or DNA from the affinity beads is effected by an elevation of temperature in the presence of a proprietary release reagent. As the quantity of beads used is very small (<1 μl), the RNA and/or DNA can be released in a final volume as low as 3 microliters. The released RNA and/or DNA is neutralized to a final volume of 5-50 microliters using a neutralization reagent and is now ready for downstream PCR.

Typically, the amount of sample introduced is about 500 microliters or less (e.g., about 250 microliters or less, about 100 microliters or less, about 50 microliters or less, about 25 microliters or less, about 10 microliters or less). In some embodiments, the amount of sample is about 2 microliters or less (e.g., about 0.5 microliters or less).

PAMAM(0) gives excellent RNA and DNA recovery, based in part on its high binding capacity, and its high release efficiency. In general, the ratio of mass of particles to the mass of RNA or DNA retained by the particles is no more than about 25 or more (e.g., no more than about 20, no more than about 10). For example, in some embodiments, about 1 gram of particles retains about 100 milligrams of RNA or DNA; when used in smaller quantities, similar ratios can be obtained (e.g., a binding capacity of 100 μg of RNA or DNA/mg beads).

Other Apparatus for DNA Capture

In other embodiments, the solid support can be configured as a retention member (e.g., porous member such as a column, filter, a porous membrane, a microporous filter, or a gel matrix, having multiple openings such as pores and/or channels, through which RNA and/or DNA passes) through which sample material (containing the RNA and/or DNA) must pass. Such a retention member may be formed of multiple surface-modified particles constrained into a suitable geometry. In some embodiments, the retention member comprises one or more filter membranes available from, for example, Osmonics, which are formed of polymers that may also be surface-modified and used to retain RNA and/or DNA. In some embodiments, a retention member is configured as a plurality of surfaces (e.g., walls or baffles) across which a sample passes. The walls or baffles are modified to retain RNA and/or DNA in preference to, e.g., PCR inhibitors. Such a retention member is typically used when the microparticles are non-magnetic.

As a sample solution moves through a processing region containing such a retention member (suitably modified to preferentially retain RNA and/or DNA), RNA and/or DNA is retained while the liquid and other solution components (e.g., inhibitors) are less retained (e.g., not retained) and exit the processing region. Typically, such a retention member retains at least about 50% of RNA and/or DNA molecules (at least about 75%, at least about 85%, at least about 90%) of the RNA and/or DNA molecules present in the sample that entered the processing region. The processing region is typically at a temperature of about 50° C. or less (e.g., 30° C. or less) during introduction of the sample. Processing can continue by washing the retention member with a wash solution to separate remaining inhibitors from RNA and/or DNA retained by the retention member.

In some embodiments, the sample preparation processes described herein are performed within a microfluidic device, such as a microfluidic cartridge configured to receive a sample, and to capture RNA and/or DNA molecules from the sample on a solid support contained within it. Exemplary microfluidic cartridges are described in U.S. Patent Application Publication No. 2006/0166233, and WO2008/061165, both of which are incorporated herein by reference. Such cartridges may include one or more actuators configured to move microdroplets of various liquid solutions within the cartridge, a chamber configured to lyse cells in the sample, and one or more channels and associated valves configured to direct, disrupt, and divert liquid flow within the cartridge.

While sample preparation has been described as being a sequence of operations carried out in a single location, such as in a process tube or a microfluidic cartridge, other configurations can be used. For example, in some embodiments, the retention member carrying a polynucleotide-affinity material can be removed from a region where DNA and/or RNA capture occurs, for subsequent processing elsewhere. For example, the retention member may be contacted with a mixture comprising DNA and/or RNA and inhibitors in one location, and then moved to another location at which the RNA and/or DNA are removed from the retention member.

Other Advantages of the DNA Capture Material Described Herein

The extraction reagents and sample preparation processes described herein offer superior performances compared to currently available off-the-shelf kits for sample preparation. Advantages of the materials and methods herein include the following.

A streamlined sample preparation procedure having fewer steps (as few as six from raw sample to purified RNA and/or DNA) and utilizing fewer containers than other procedures.

Extraction control (cellular, plasmid, or naked) DNA can also be included along with the affinity beads. An internal control DNA can be included with the lysis reagents so that the internal control DNA gets co-purified with the other DNA (such as the target DNA) present in the clinical sample, and gets eluted amongst the final released DNA. During amplification of the eluted DNA, the internal control DNA is also amplified, and can subsequently be detected using a separate fluorophore from the target DNA. This gives an extra confirmation that the sample prep process worked as required.

The description herein has included a characterization of properties and use of microparticles coated in PAMAM (Generation 0). It would be understood by one of ordinary skill in the art that other affinity molecules may suitably be used in the processes described herein, as described elsewhere (e.g., U.S. patent application publication 2006-0166233, incorporated herein by reference).

EXAMPLES

Example 1

Sample Preparation Process

The following six steps can be accomplished in as little as 20 minutes for a single sample, to 30 minutes for a batch of 12 samples, using a reagent kit as further described herein. The steps are also easily automated as in a system described in U.S. provisional patent application Ser. No. 60/959,437, filed Jul. 13, 2007, incorporated herein by reference. The steps are also shown, schematically, in FIG. 1, and described elsewhere herein.

One exemplary process is as follows.

1. Mix ~500 µl of the clinical sample with 500 µl of lysis buffer and magnetic affinity beads, surface-bound with PAMAM(0). Kits for detecting viruses such as EV13 include some lytic enzymes as well dissolved in the lysis buffer.

2. Incubate the mixture of sample, lysis buffer, and beads at a temperature between room temperature and 60° C. for 5-10 minutes, to lys the cells and bind the RNA and/or DNA to the affinity beads.

3. Separate the magnetic beads and remove as much of the supernatant solution as possible.

4. Wash the beads with a wash reagent.

5. Release the RNA and/or DNA from the beads by heating the beads for 3 minutes at 85° C. in the presence of as little as 3 microliters of release solution.

6. Remove the released RNA and/or DNA and neutralize the solution with a neutralization reagent, such as a Tris buffer, to create PCR-ready RNA and/or DNA.

Another exemplary process is as follows.

Sample: Mix 500 µl Plasma w 500 µl Prep Buffer, or Dip Swab in 1 mL RNA Prep Buffer.

The mixture may optionally be pre-filtered.

Incubate @ 60° C. for 10 min.; clean up with proteolytic enzymes if necessary (swab only) and effect RNA and/or DNA capture by PAMAM(G0) coated affinity beads (magnetic) as further described herein.

Optionally, in a case where RNA is desired to be determined, apply DNAse treatment (such as with 7U DNase @ 37 deg C. for 10 min.) to the mixture.

Wash RNA bound beads with 100 µl Wash Reagent (2×) as further described herein.

Release RNA from beads with heat (85° C.; 3 min.) in the presence of Release Reagent, as further described herein, thereby liberating RT-PCR ready RNA.

Example 2

Application to a Wide Variety of Matrices

The procedures described herein work for a variety of sample matrices, including both clinical and non-clinical samples, as shown by the following non-exhaustive list:

Nasal swab
CSF
Nasal swab in M4
Nasal swab in UTM
Plasma

Example 3

Representative Results

Figure 3:
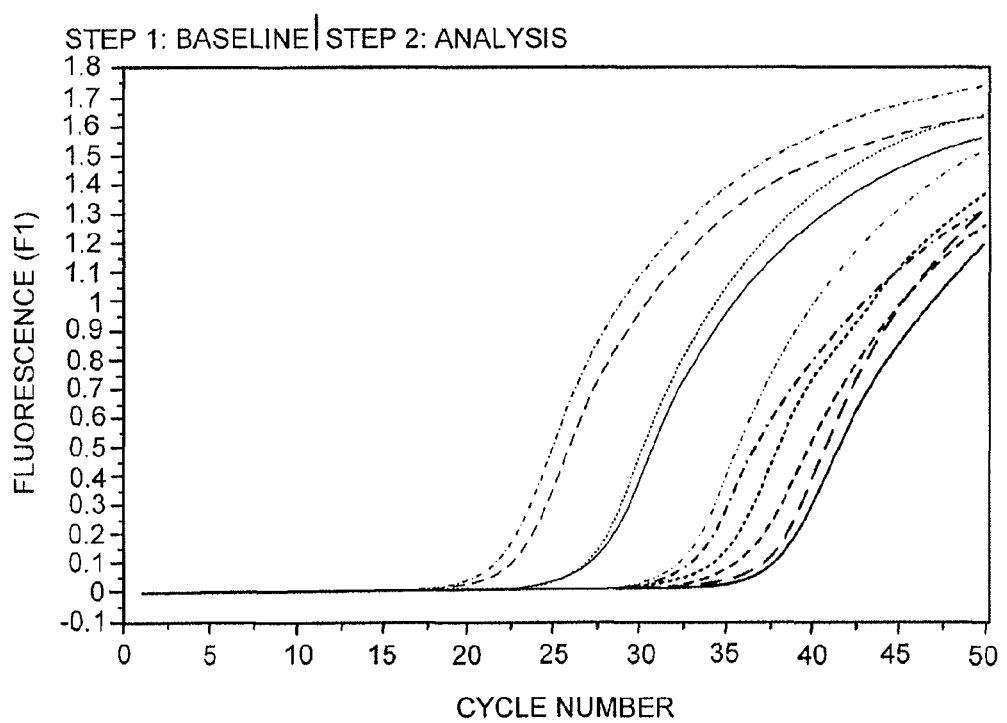
FIG. 3 shows PCR curves for EV13 RNA extraction from nasal swabs.

FIG. 3 shows the use of RNA extraction reagent, PAMAM (0), and a process as further described herein, to isolate and purify Enterovirus 13 (EV13) RNA from Nasal Swabs, using a lysis buffer as described elsewhere herein. The graph shows PCR curves for various samples spiked with each of $2\times10^4$, 2000, 200, 50, and 20 copies/1 mL of RNA Prep buffer. The RNA was released into 10 µl, but only 2 µl of released RNA was used for RT-PCR, which was performed using a Qiagen RT-PCR kit. PCR curves rise from the axis in order of decreasing concentration, from left to right.

Figure 4:
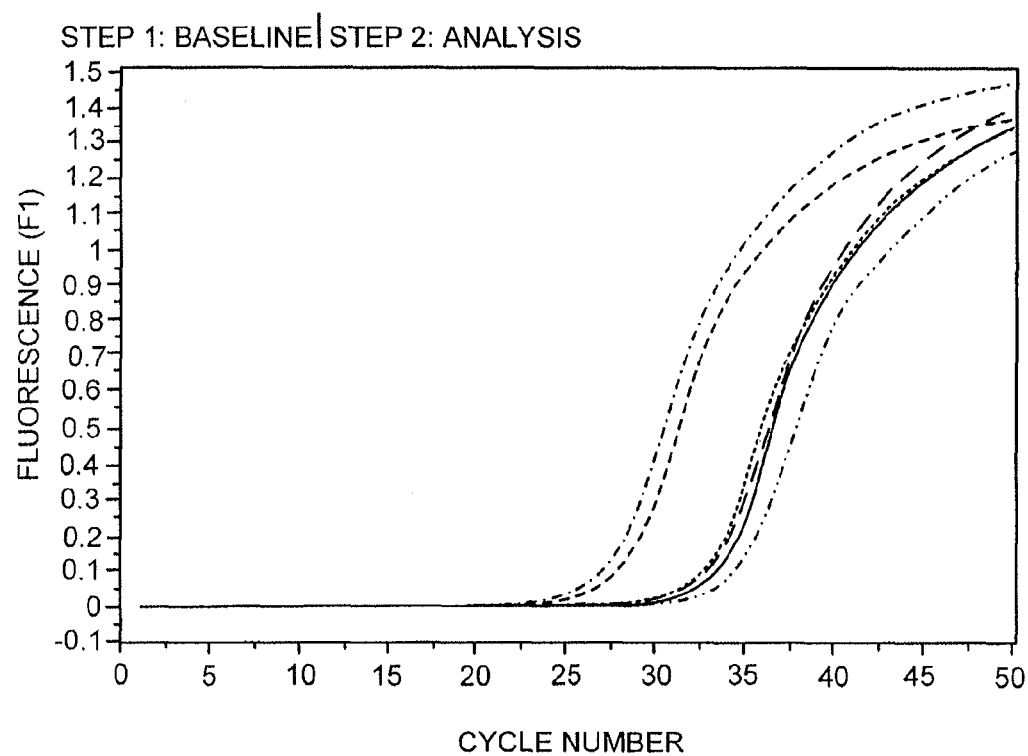
FIG. 4 shows PCR curves for EV13 RNA extraction in M4 media.

FIG. 4 shows the use of RNA extraction reagent, PAMAM (0), and a process as further described herein, to isolate and purify Enterovirus 13 (EV13) RNA from Nasal Swabs collected in M4 media. The graph shows PCR curves for various samples spiked with each of 1000, 100, and 50, copies/1 mL of sample. PCR curves rise from the axis in order of decreasing concentration, from left to right.

Figure 5:
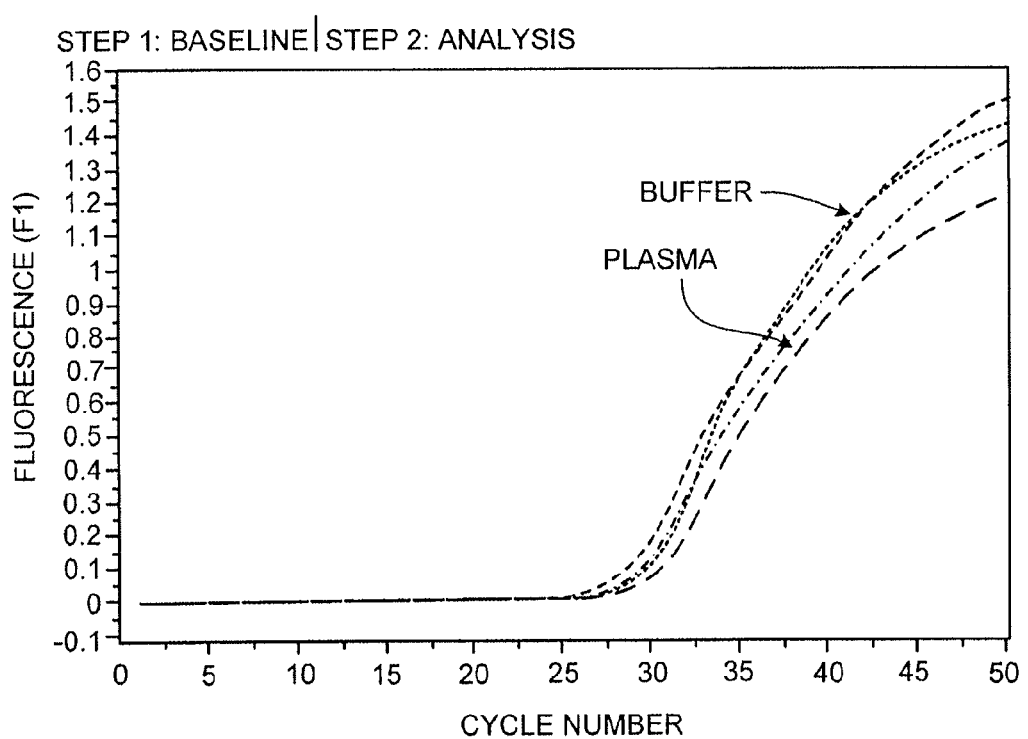
FIG. 5 shows a comparison of PCR curves from RNA extracted from a buffer to one obtained from plasma.

FIG. 5 shows a comparison of RNA extraction using PAMAM(0) beads between buffer samples and plasma. 500 copies of EV13 RNA per 1 mL were used in both buffer and plasma samples, according to a process as further described herein.

Figure 6:
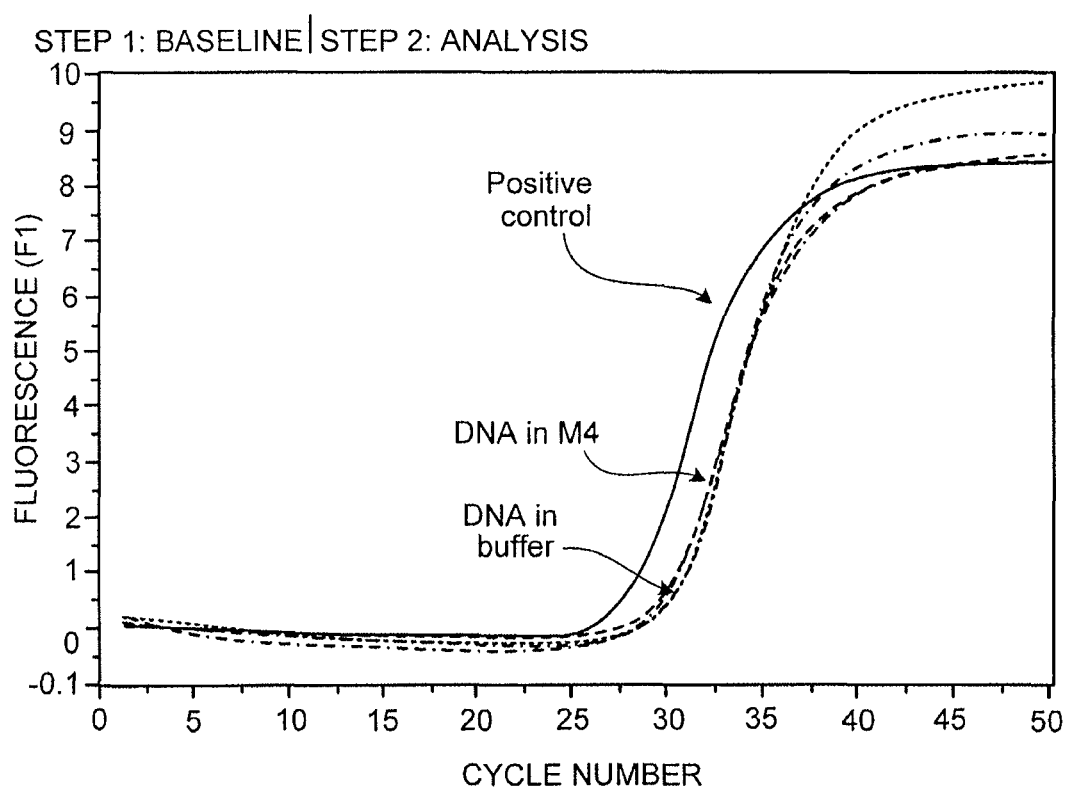
FIG. 6 shows RNA extraction using beads.

FIG. 6 shows extraction of DNA, using PAMAM(0) beads. 2.5 pg DNA spiked into an M4 buffer, or a lysis buffer as described herein, were extracted using a process for extracting RNA from an M4 collection buffer as further described herein.

Figure 7:
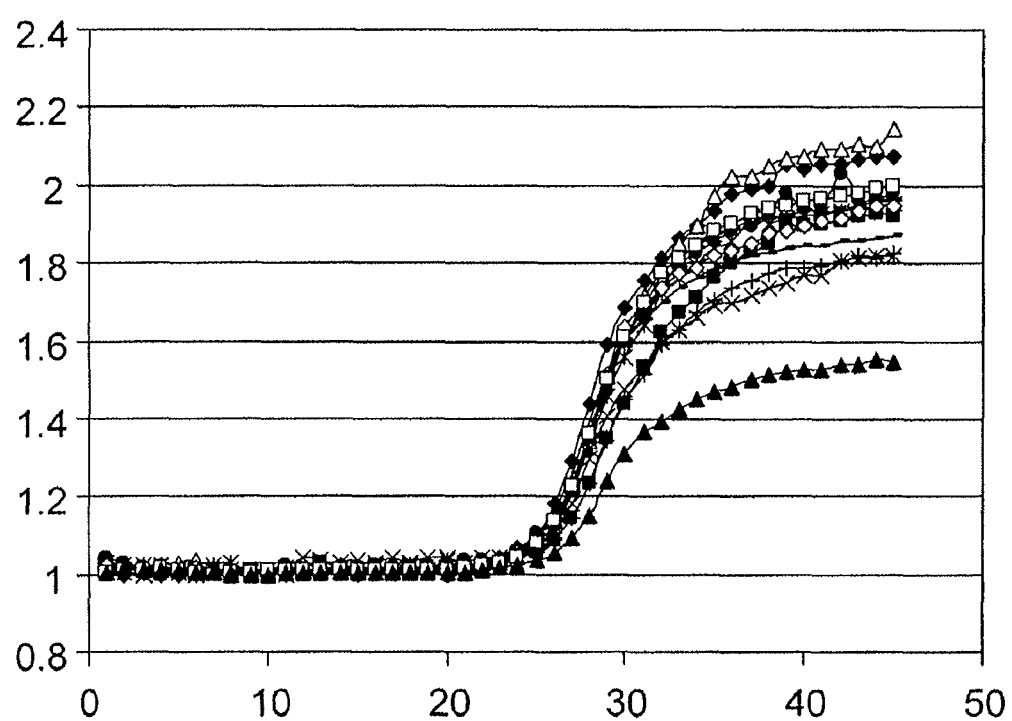
FIG. 7 shows RNA extraction from plasma.

FIG. 7 shows PCR curves for RNA extraction from a 500 µl plasma sample containing 200 copies EV13 RNA, using 7U DNAse treatment.

Figure 8:
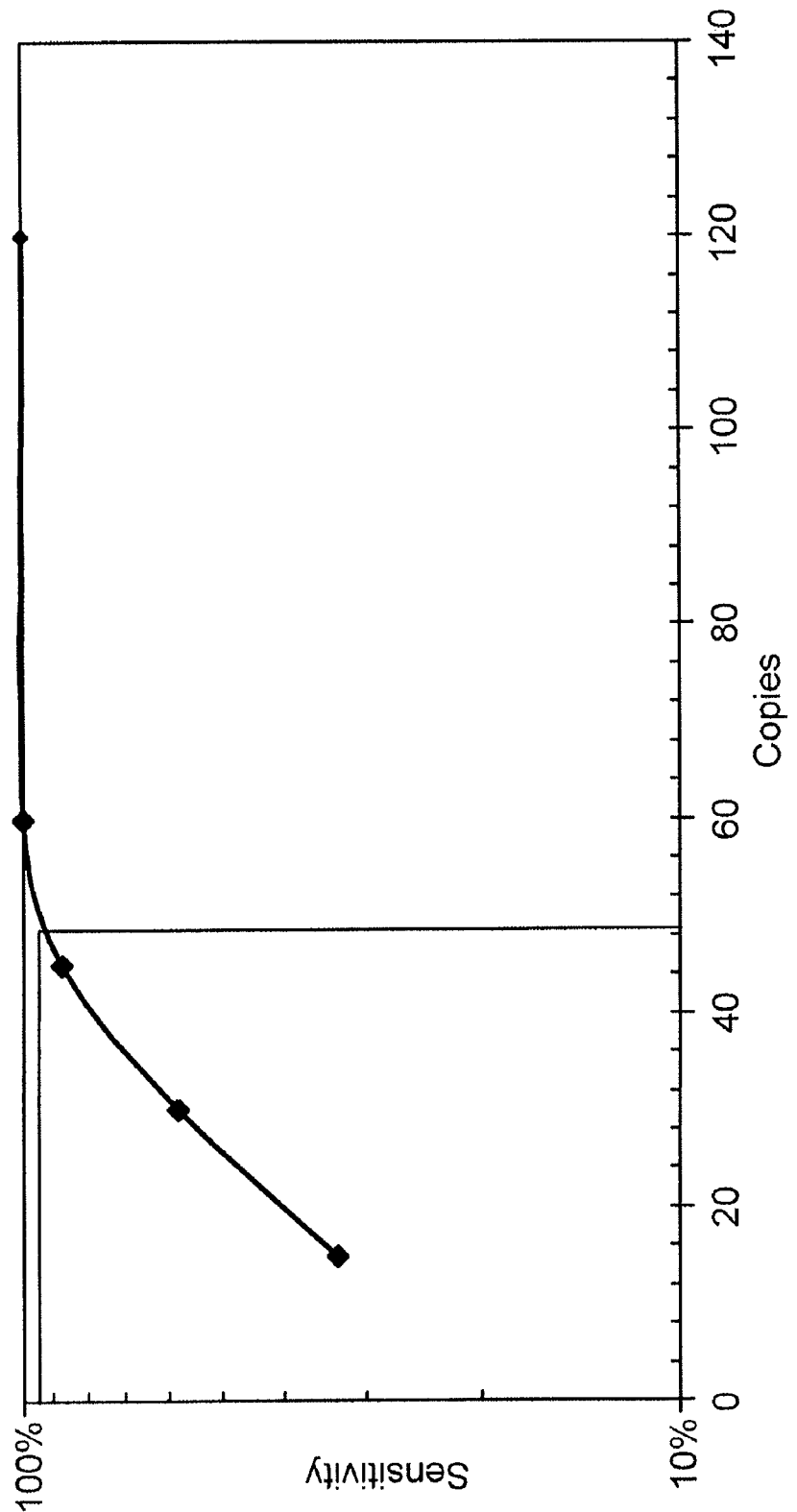
FIG. 8 illustrates extraction sensitivity.

FIG. 8 shows illustrates the sensitivity of the process. Process analysis reveals an LoD of 50 copies/200 µl CSF.

Example 4

Exemplary Protocol for the Extraction of RNA from M4, Dry Swab in 1×TCEP Buffer, THB Samples Sample Preparation Pre-Processing (Only Swab Samples Require Filtration)

| Step | Action |
|---|---|
| 1 | Pipette 500 µL of specimen into a tube (1.7 ml DOT snap cap tube) containing 500 µL of TCEP buffer |
| 2 | Pipette up and down 2x, and then pipette entire amount into 3 ml syringe |
| 3 | Insert plunger into syringe, and filter contents into a clean tube (1.7 ml DOT snap cap tube), applying pressure until all liquid is expelled, and foam starts to come out of filter (avoid getting foam into sample). |

RNA Extraction and PCR Prep

| Step | Action |
|---|---|
| 1 | Pipette sample (500 µL of specimen, plus 500 µL TCEP buffer) into a 1.7 ml DOT snap cap tube containing 30 µL of RNA magnetic beads. Cap and invert Reaction Tube 5 times, or until beads are dispersed (or dissolved, in the case of lyophilized beads). |
| 2 | Immediately place samples in a 60° C. water bath, and incubate for 10 min (10.5 min maximum). |
| 3 | Remove samples from water bath, and dry outsides of tubes with a Absorbent wipe. |
| 4 | Place tubes on magnetic rack, and allow separation to proceed for 1 minute (1.5 min max). |
| 5 | Using a fresh pipette for each sample, carefully aspirate 1 ml of supernatant from each sample (without disturbing beads), using a 1 ml pipettor. Discard supernatant. Be sure to remove any liquid that remains in the tube cap. |
| 6 | After initial removal of supernatants from all samples, remove any remaining liquid using a fresh 1 ml pipette tip for each sample. |
| 7 | Place tubes in a non-magnetic tube rack, and add 100 µL of Wash Buffer (0.1 mM Tris, pH 7.5) to each tube using a 200 ul pipette tip. Pipette up and down 10 times, or until all magnetic beads are resuspended, and no beads remain stuck to pipette tip. |
| 8 | Place tubes on magnetic rack for 30 seconds, allowing beads to separate. |
| 9 | Carefully aspirate supernatant from all samples using a 200 ul pipette tip. Discard Supernatant. Using a fresh 20 µl tip for each sample, aspirate any remaining liquid left in the sample (ie-liquid that has "settled" following the first aspiration step), and discard the liquid. |
| 10 | Place tubes in a non-magnetic tube rack, and add 10 µL of Release Buffer (20 mM Bis-Tris Propane or 20 mM Tris pH 9). Vortex for 10 seconds, or until beads are resuspended. |
| 11 | Place samples in a heat block at 85° C. for 3 minutes (3.5 min max). Remove samples from heat block, and place on magnetic rack for 30 seconds (1 min max). |
| 12 | Remove samples from heat block, and place on magnetic rack for 30 seconds (1 min max). |
| 13 | Keeping tubes on the magnetic rack, remove all liquid, carefully avoiding magnetic beads on side of tube, and place in 0.65 ml DOT tube. |
| 14 | Mix sample by pipetting up and down once. Sample is now ready for PCR. |
| 15 | Make PCR mix using Quantitect kit spiked with 0.6uM primers and extra platinum taq. |
| 16 | Add 8 uL of mix into Rotorgene or LC capillaries, add 2 µL of RNA. |
| 17 | Run RT PCR program as follows: 50 degrees for 20 min (RT step), 95 degrees for 5 min (denaturation), cycling at 95-2 sec, 58-50 sec (50 cycles). |

Example 5

Exemplary Protocol for the Extraction of RNA from Plasma Samples

RNA Extraction and PCR Prep

| Step | Action |
|---|---|
| 1 | Pipette sample (500 ul of specimen, plus 500 ul TCEP buffer + 70 uL 10% SDS) into a 1.7 ml DOT snap cap tube containing 30 ul of RNA magnetic beads. Cap and invert Reaction Tube 5 times, or until beads are dispersed (or dissolved, in the case of lyophilized beads). |
| 2 | Immediately place samples in a 60° C. water bath, and incubate for 10 min (10.5 min maximum). |
| 3 | Remove samples from water bath, and dry outsides of tubes with a Absorbent wipe. |
| 4 | Place tubes on magnetic rack, and allow separation to proceed for 1 minute (1.5 min max). |
| 5 | Using a fresh pipette for each sample, carefully aspirate 1 ml of supernatant from each sample (without disturbing beads), using a 1 ml pipettor. Discard supernatant. Be sure to remove any liquid that remains in the tube cap. |
| 6 | After initial removal of supernatants from all samples, remove any remaining liquid using a fresh 1 ml pipette tip for each sample. |
| 7 | Add 250 uL DNAse buffer with 1 Dnase pellet or 5 units of liquid DNAse. Resuspend beads by vortexing or pipetting. |
| 8 | Incubate at 37 for 10 min. |
| 9 | Place tubes on magnetic rack, and allow separation to proceed for 1 minute (1.5 min max). |
| 10 | Using a fresh pipette for each sample, carefully aspirate 1 ml of supernatant from each sample (without disturbing beads), using a 1 ml pipettor. Discard supernatant. Be sure to remove any liquid that remains in the tube cap. |
| 11 | Place tubes in a non-magnetic tube rack, and add 100 μl of Wash Buffer (0.1 mM Tris, pH 7.5) to each tube using a 200 ul pipette tip. Pipette up and down 10 times, or until all magnetic beads are resuspended, and no beads remain stuck to pipette tip. |
| 12 | Place tubes on magnetic rack for 30 seconds, allowing beads to separate. |
| 13 | Carefully aspirate supernatant from all samples using a 200 ul pipette tip. Discard Supernatant. Using a fresh 20 ul tip for each sample, aspirate any remaining liquid left in the sample (ie-liquid that has "settled" following the first aspiration step), and discard the liquid. |
| 14 | Place tubes in a non-magnetic tube rack, and add 10 μL of Release Buffer (20 mM Bis-Tris Propane or 20 mM Tris pH 9). Vortex for 10 seconds, or until beads are resuspended. |
| 15 | Place samples in a heat block at 85° C. for 3 minutes (3.5 min max). |
| 16 | Remove samples from heat block, and place on magnetic rack for 30 seconds (1 min max). |
| 17 | Keeping tubes on the magnetic rack, remove all liquid, carefully avoiding magnetic beads on side of tube, and place in 0.65 ml DOT tube. |
| 18 | Mix sample by pipetting up and down once. Sample is now ready for PCR. |
| 19 | Make PCR mix using Quantitect kit spiked with 0.6uM primers and extra platinum taq. |
| 20 | Add 8 uL of mix into Rotorgene or LC capillaries, add 2 uL of RNA. |
| 21 | Run RT PCR program as follows: 50 degrees for 20 min (RT step), 95 degrees for 5 min (denaturation), cycling at 95-2 sec, 58-50 sec (50 cycles). |

Example 6

Assembly Process for 2×TCEP Buffer for RNA Extractions

The procedure in this example provides a method appropriate for preparing up to 50 mL of a 2×TCEP Buffer (20 mM Tris HCl pH 7.0, 2% Tx-100, 10 mM TCEP) used in RNA extractions, as further described herein. The following is a list of reagents utilized in the process.

1 M Tris-HCl pH 7.0
100% Triton X-100 ('Tx-100')
TCEP (Tris(2-carboxyethyl)phosphine hydrochloride)
Ultrapure Water The following is a list of equipment utilized in the process.

Laminar flow hood
Serological pipette filler
Serological pipette
Vortexer
Appropriate size container
New, sterile graduated cylinder
Appropriate Personal Protective Equipment (PPE)
Product Label An operator performing this procedure must know how to prepare buffers, and possess an excellent pipetting technique, and should exercise general lab sterile techniques, prepare the solution in a laminar flow hood for sterility, and be cautious to not contaminate stock reagents. Gloves and lab coat should be worn by operator at all times.

Preparation of 50 mL of the 2×TCEP Buffer (20 mM Tris HCl pH 7.0, 2% Tx-100, 10 mM TCEP)

| Step | Action | For 50 mls |
|---|---|---|
| 1 | Verify reagent availability and expiration. Also perform a visual inspection of stock reagents. | |
| 2 | Affix the product label to the appropriate container. | |
| 3 | Using a serological pipette or a new graduated cylinder dispense ultrapure water into the container. | 45 mL H2O |
| 4 | Using a serological pipette or a new graduated cylinder, 1 mL Tris-HCl dispense 1M Tris-HCl pH 7.0 into container. | 1M Tris-HCl |
| 5 | Weigh out appropriate amount of TCEP and add to container. | 143 mg |

-continued

| Step | Action | For 50 mls |
|---|---|---|
| 6 | Vortex/shake well to mix. Do not add Triton until the TCEP has completely dissolved. | |
| 7 | Using a serological pipette, add Triton X-100 to container being careful to get all of solution out of pipette. | 4 mL |
| 8 | Vortex/shake well to mix. | |
| 9 | Store at room temperature. | |

Example 7

Exemplary Process for the Preparation of Magnetic RNA Affinity Microspheres

Figure 9:
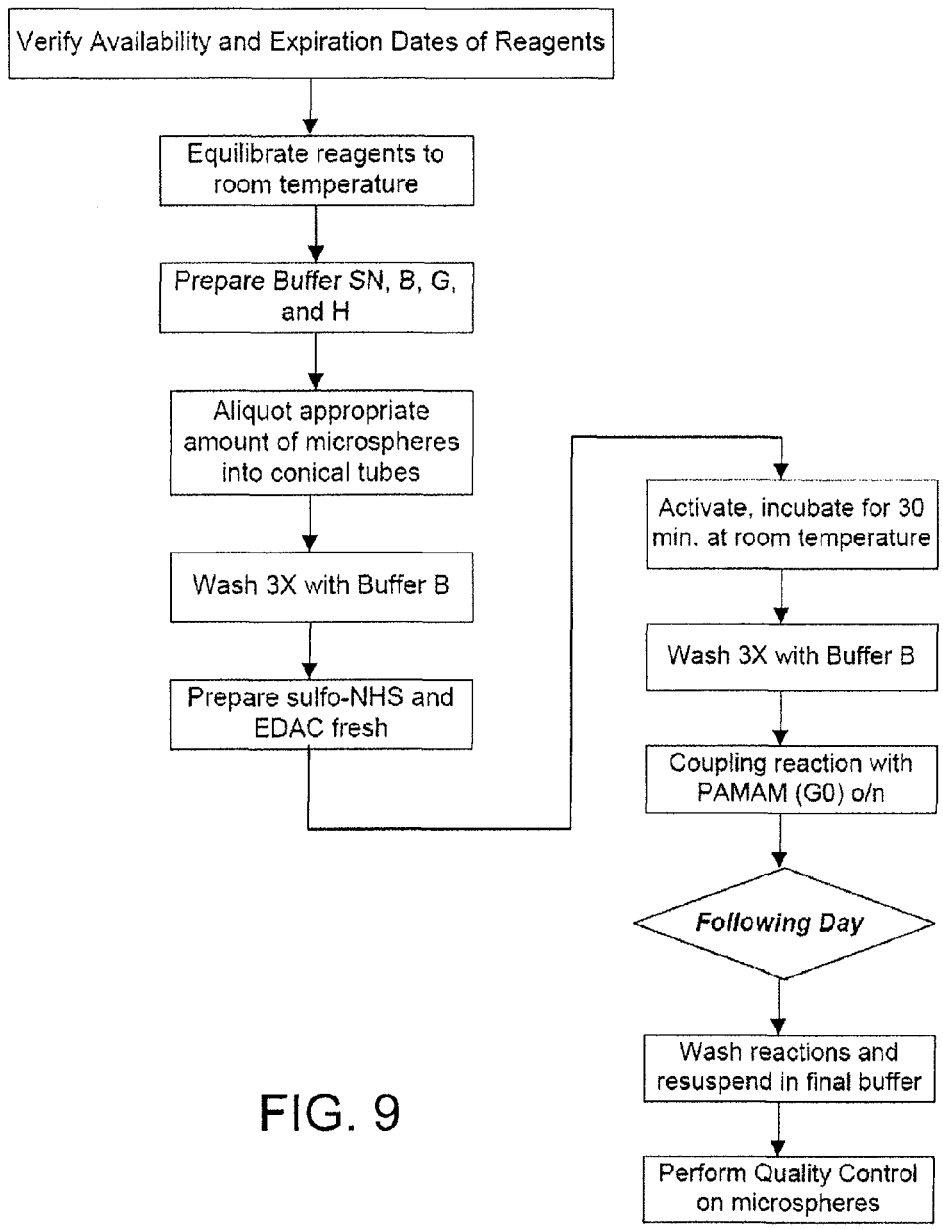
FIG. 9 shows a flow-chart for a process of making PAMAM (Generation 0) coated microparticles.

This procedure provides an appropriate method for one batch of PAMAM(G0) coated magnetic microspheres, commonly referred to as Magnetic RNA-Affinity Microspheres. One batch consists of 1-10 ml synthesis resulting in 6 mL of magnetic RNA affinity microspheres. A flow-chart of the process is shown in FIG. 9. The following is a list of equipment utilized in the process.

Vortexer
Microcentrifuge
Magnetic Rack
1.7 mL microcentrifuge tubes
4-oz specimen containers
50 mL conical tubes
15 mL conical tubes
Centrifuge
pH meter
Pipettors
Pipettor tips
Ultrasonic dismembrator
dH20 wash bottle
Task Wipers
Balance
Laboratory marker
Gloves and Labcoat
Orbital shaker
Labeling tape
Pipette filler
Serological pipettes An operator performing this procedure must be competent with a microbalance, pipettors, pH meter, ultrasonic dimembrator and a microcentrifuge, and must know how to prepare buffers and possess an excellent pipetting technique. Gloves, labcoat, and eye protection should be worn by the operator at all times. Ear protection must be worn during sonication steps. All solutions are prepared in a laminar flow hood.

Procedure—Preparation of Buffers

| Step | Action |
|---|---|
| 1 | Verify availability and check expiration dates of all solutions and reagents. |
| 2 | Visually inspect all stock solutions and reagents for precipitation or color change. Do not use if precipitation occurs or color changes. |
| 3 | Equilibrate all aliquoted stock solutions and reagents to RT. Take out EDAC and NHS from −20° C. and equilibrate to RT before use, this should take approximately one hour. |

Preparation of 70 mL Buffer SN-B (50 mM MES Buffer pH 6.1, 0.15% Triton X-100)

| Step | Action | For 70 mls |
|---|---|---|
| 1 | Label a 4-oz or 500 ml container with "Buffer SN-B", date, and initials. | |
| 2 | Using a serological pipette Buffer SN-C to bottle. | 7 mL |
| 3 | With a P5000, 10% Triton X-100 to bottle. | 420 uL |
| 4 | Using a graduated cylinder, add ultrapure water to bottle. | 62.5 mL |
| 5 | Mix well by inversion. | |
| 6 | Check pH of solution, which should be between 5.8-6.5. | |
| 7 | Store at 4° C. during overnight incubation but discard after lot manufacture is complete. | |

Preparation of 50 mL Buffer SN-G (50 mM Tris pH 7.5, 0.1% Triton X-100)

| Step | Action | For 50 mls |
|---|---|---|
| 1 | Labe a 50 mL conical tube with "Buffer SN-G", date, and initials | |
| 2 | Using a serological pipette add 1M Tris pH 7.5 to bottle | 2.5 mL |
| 3 | With a P5000, 10% Triton X-100 to bottle. | 200 uL |
| 4 | Using a graduated cylinder, add ultrapure water to bottle. | 47.3 mL |
| 5 | Mix well by inversion. | |
| 6 | Chek pH of solution, which should be between 7.2-7.7 | |
| 7 | Store at RT for the duration of lot manufacture but discard after lot manufacture is complete. | |

Preparation of 10 mL Buffer SN-H (50 mM MES pH 6.1, no Tx)

| Step | Action | For 10 mls |
|---|---|---|
| 1 | Label a 15 mL conical tube with "Buffer SN-H", date, and initials. | |
| 2 | Using a serological pipette add Buffer C to bottle | 1 mL |
| 3 | Using a graduated cylinder, add ultrapure water to bottle. | 9 mL |
| 4 | Mix well by inversion. | |
| 5 | Check pH of solution, which should be between 5.8-6.5 | |
| 6 | Store at RT for the duration of lot manufacture but discard after lot manufacture is complete. | |

Steps to be performed on Day 1, include the following.

| Step | Action |
|---|---|
| 1 | Calculate required amount of carboxylated microspheres. Divide 10 mL by % solids to calculate amount of microspheres needed per reaction. 5 reactions per set. Multiply this number by 5 to get the total amount of microspheres for the full set. |
| 2 | Vortex the vial containing the microspheres very well (for approx 1 minute). |
| 3 | Label 1-50 mL conical tubes with Lot number, date, and initials. |
| 4 | Pipette the appropriate amount of microspheres into 50 mL conical tube. |
| 5 | Place conical tubes onto magnetic rack and let sit until beads are fully captured by magnet. Remove supernatant carefully. |

| | | |
|---|---|---|
| MES buffer wash | | For 30 mls |
| 6 | Add Buffer SN-B to each tube and vortex to mix | 10 mls |
| | Place conical tubes onto magnetic rack and let sit until beads are fully captured by magnet. | |
| | Remove supernatant carefully. Repeat wash 2 more times. | |
| Prepare sulfo-NHS | | |
| 7 | Weigh out small amount of sulfo-NHS on weigh paper and multiply weight (in mg) by 20 to calculate μL of ultrapure water to add to make 50 mg/ml solution. | |
| | Need 1.5 mL for 1 reactions (75 mg). | |
| | Add to 1.7 mL tube and mix well. | |
| | Weight (mg) × 20 = μL ultrapure water needed. | |
| | Add ultrapure water and vortex well to resuspend. | |
| | NHS solution should be prepared right before use, discard after 15 min. | |
| For 30 mls Activation (Prepare EDAC in hood) | | |
| 8 | Add reagents in the following order to each conical tube: | For 30 mls |
| | (i) dd$H_2O$ | 5000 μL |
| | (ii) Buffer SN-C | 1000 μL |
| | (iii) 50 mg/mL sulfo-NHS | 1500 μL |
| | Sonicate using ultrasonic dismembrator at a power output of 12 for the appropriate time making sure that the probe is submerged at all time. Clean probe with d$H_2O$ and wipe with absorbent wipe before and after sonication. | 10 seconds |
| 9 | Immediately prepare 5 mg/ml EDAC in hood. EDAC solution should be prepared right before use, discard after 15 min. Weigh out small amount of EDAC onto weigh paper and multiply weight (in mg) by 200 to calculate μL of ultrapure water needed to make 5 mg/ml solution. | |
| | Need 2480 μl total (12.4 mg). | |
| | Prepare in 50 mL conical tube. | |
| | Weight (mg) × 200 = (μL) ultrapure water to add. | |
| | Vortex well after addition of ultrapure H2O. | |
| 10 | Add the following: | |
| | (i) 10% Triton X-100 10 μL | 10 μL |
| | (ii) 5 mg/mL EDAC (add EDAC solution carefully; drop by drop 2480 μL while vortexing the solution at very low speed) | 2480 μL |
| | (iii) 50 mg/mL sulfo-NHS | 1500 μL |
| Mix well by vortexing. | | |
| 11 | Record number of times EDAC opened on bottle. Discard after 5 uses. | |
| 12 | Secure tubes to orbital shaker with labeling tape and incubate at room temperature at setting 6 (or at setting where microspheres are mixing well). | 30 mins. |
| 13 | After incubation, centrifuge for 5 min at maximum speed and then place on magnet. Remove supernatant carefully but completely. | 5 mins. |
| MES buffer wash | | For 30 mls |
| 14 | Add Buffer SN-B to each tube and vortex to mix | 10 mls |
| | Place conical tubes onto magnetic rack and let sit until beads are fully captured by magnet. Remove supernatant carefully. Repeat wash 2 more times. | |
| Coupling | | |
| 15 | Prepare coupling reaction: | For 10 mls |
| | (i) Add Buffer H | 6 mL |
| | Sonicate using ultrasonic dismembrator at power output 9 for the appropriate time making sure that the probe is submerged. Clean probe with d$H_2O$ and wipe with absorbent wipe before and after sonication. | 10 sec |
| | (ii) Add PAMAM(G0) (add solution carefully, drop by drop while vortexing the solution on low speed). | 250 μL |
| | (iii) Mix by vortexing | |
| 16 | Secure tube to orbital shaker with labeling tape. Incubate overnight at a setting of 6 at room temperature (or at setting where microspheres are mixing well). | |
| 17 | Store buffers SN-B, H and G at 4° C. overnight. | |
| | Return NHS and EDAC stocks to −20° C. Return buffer SN-C to 4° C. | |

Steps to be performed on Day 2, include the following.

| Step | Action | For 30 mls |
|---|---|---|
| 18 | After overnight incubation, remove buffers SN-B and G from 4° C. and equilibrate to RT (approximately 1 hr). | |
| 19 | Centrifuge tubes for 5 min at maximum speed and place on magnetic rack. Remove supernatant carefully but completely. | |
| Tri Washes | | |
| 20 | Add Buffer SN G to each tube and vortex to mix. Clean probe with dH20 and wipe with absorbent wipe before and after sonication. Place conical tubes onto magnetic rack and let sit until beads are fully captured by magnet. Remove supernatant carefully. Repeat wash 2 more times. | 10 mL |
| Final Resuspension | | |
| 21 | Resuspend each reaction in Buffer SN-B by sonication using ultrasonic dismembrator at power output of 12 for 10 seconds (ensure that probe is submerged). Clean probe with dH2O and wipe with absorbent wipe before and after sonication. | 6 mL |
| 22 | Affix appropriate label to tube. | |
| 23 | Discard all buffers. Store Buffer SN-C at 4° C. | |
| 25 | Store at 4° C. Stable for 1 month if stored appropriately. | |

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed is:

1. A method for isolating polynucleotides from a cell-containing sample in a process tube, the method comprising:
   contacting the sample in the process tube with a lysis solution having a pH between 4 and 8, thereby releasing polynucleotides from the cells in the cell-containing sample;
   contacting the sample in the process tube with a plurality of magnetic binding particles coated in PAMAM, wherein the polynucleotides become reversibly bound to the PAMAM, thereby creating binding particles bound with polynucleotides and a solution containing residual cellular material in the process tube;
   compacting the binding particles bound with the polynucleotides in the process tube by positioning a magnet in communication with the binding particles;
   removing the solution containing residual cellular material from the process tube;
   washing the binding particles with a solution having a pH≤9, thereby retaining the polynucleotides bound to the binding particles; and
   contacting the binding particles bound with polynucleotides with a solution having a pH ≥9 to release the polynucleotides from the PAMAM on the binding particles, thereby isolating the polynucleotides from the cell-containing sample.

2. The method of claim 1, wherein the PAMAM on the binding particles comprises PAMAM(Generation 0).

3. The method of claim 1, wherein the polynucleotides comprise a mixture of DNA and RNA molecules.

4. The method of claim 1, wherein the contacting the compacted binding particles with a release solution further comprises contacting the binding particles with a first release solution having a pH in the range 9-12, thereby releasing any bound RNA from the PAMAM on the binding particles, while retaining any bound DNA on the binding particles.

5. The method of claim 4, wherein the contacting the binding particles with a release solution further comprises contacting the binding particles bound by polynucleotides with a second release solution having a pH in the range 12-14, thereby releasing bound DNA from the PAMAM on the binding particles.

6. The method of claim 1, wherein the binding particles are a polymeric material, the polymeric material selected from the group consisting of: polystyrene, latex polymers, polyacrylamide, and polyethylene oxide.

7. The method of claim 6, further wherein the polymeric material comprises one or more carboxylic groups to which the PAMAM is covalently linked.

8. A method for separately isolating DNA and RNA from a cell-containing sample, the method comprising:
   contacting the sample with a lysis solution having a pH between 4 and 8, thereby releasing DNA and RNA from the cells in the cell-containing sample;
   contacting the sample with a plurality of binding particles, wherein the binding particles retain the DNA and RNA in the cell-containing sample;
   compacting the plurality of binding particles having the DNA and RNA bound thereto;
   releasing the RNA from the binding particles by contacting the compacted binding particles with a first release solution;
   removing the solution containing the released RNA, thereby isolating the RNA; and
   releasing the DNA from the binding particles by contacting the compacted binding particles with a second release solution, thereby isolating the DNA, wherein the pH of the second release solution is greater than the pH of the first release solution.

9. The method of claim 8, wherein the binding particles are coated in PAMAM.

10. The method of claim 9, wherein the PAMAM on the binding particles comprises PAMAM(Generation 0).

11. The method of claim 8, wherein the first release solution has a pH of 9-12.

12. The method of claim 8, wherein the second release solution has a pH of 12-14.

* * * * *